(12) United States Patent
Someya et al.

(10) Patent No.: US 12,139,646 B2
(45) Date of Patent: Nov. 12, 2024

(54) COMPOUND, RESIN PRECURSOR, CURED OBJECT, OPTICAL ELEMENT, OPTICAL SYSTEM, INTERCHANGEABLE CAMERA LENS, OPTICAL DEVICE, CEMENTED LENS, AND METHOD FOR MANUFACTURING CEMENTED LENS

(71) Applicant: NIKON CORPORATION, Tokyo (JP)

(72) Inventors: Yoshihiro Someya, Yamato (JP); Masayuki Shijo, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 819 days.

(21) Appl. No.: 17/314,230

(22) Filed: May 7, 2021

(65) Prior Publication Data

US 2021/0395580 A1 Dec. 23, 2021

Related U.S. Application Data

(63) Continuation of application No. PCT/JP2018/041695, filed on Nov. 9, 2018.

(51) Int. Cl.
| | |
|---|---|
| *C09J 4/00* | (2006.01) |
| *C07C 69/54* | (2006.01) |
| *C07C 69/593* | (2006.01) |
| *C07C 69/653* | (2006.01) |
| *C08F 220/10* | (2006.01) |
| *C08F 220/22* | (2006.01) |
| *C08F 220/26* | (2006.01) |
| *C08F 220/30* | (2006.01) |
| *C09J 5/00* | (2006.01) |

(Continued)

(52) U.S. Cl.
CPC .............. *C09J 133/16* (2013.01); *C07C 69/54* (2013.01); *C07C 69/653* (2013.01); *C08F 220/302* (2020.02); *C09J 4/00* (2013.01); *C09J 5/00* (2013.01); *G02B 1/041* (2013.01); *G02B 13/006* (2013.01); *C08F 2800/10* (2013.01); *C09J 2433/00* (2013.01)

(58) Field of Classification Search
CPC .... C08J 4/00; C08J 133/16; C08J 5/04; C08F 220/10; C08F 220/22; C08F 220/26; C07C 69/593; G02B 1/04; G02B 13/002; C09J 4/00; C09J 133/16; C09J 5/04
See application file for complete search history.

(56) References Cited

FOREIGN PATENT DOCUMENTS

JP 2016-95542 5/2016

OTHER PUBLICATIONS

International Searhc Report, PCT/ISA/210, dated Feb. 12, 2019 in corresponding International Patent Application No. PCT/JP2018/041695.

(Continued)

*Primary Examiner* — Caixia Lu

(57) ABSTRACT

Provided is a compound represented by Formula (1) given below. (In the formula, $R^1$ represents a hydrogen atom or a methyl group, $R^2$ represents a hydrogen atom, a phenyl group, a $C_{1\ to\ 8}$ alkyl group, or a $C_{1\ to\ 4}$ perfluoroalkyl group, $X^1$ represents a hydrogen atom or a hydroxy group, $Y^1$ represents a $C_{1\ to\ 9}$ alkylene group containing a fluorine atom or a $C_{1\ to\ 9}$ alkylene group containing no fluorine atom, and $n^1$ is an integer from 0 to 3.).

23 Claims, 5 Drawing Sheets

(51) Int. Cl.
*C09J 5/04* (2006.01)
*C09J 133/16* (2006.01)
*G02B 1/04* (2006.01)
*G02B 13/00* (2006.01)

(56) References Cited

OTHER PUBLICATIONS

Written Opinion of the International Searching Authority, PCT/ISA/237, dated Feb. 12, 2019, in corresponding International Patent Application No. PCT/JP2018/041695.

COMPOUND, RESIN PRECURSOR, CURED OBJECT, OPTICAL ELEMENT, OPTICAL SYSTEM, INTERCHANGEABLE CAMERA LENS, OPTICAL DEVICE, CEMENTED LENS, AND METHOD FOR MANUFACTURING CEMENTED LENS

TECHNICAL FIELD

The present invention relates to a compound, a resin precursor, a cured object, and optical element, an optical system, an interchangeable camera lens, an optical device, a cemented lens, and a method for manufacturing cemented lens.

BACKGROUND ART

For example, Patent Literature 1 discloses a cemented lens obtained by adhering an object-side lens having negative power and an image-side lens having positive power by using a resin adhesive layer. For satisfactory correction of chromatic aberrations, a material having a large $\theta_{g,F}$ value is demanded for the resin adhesive layer used in such cemented lens.

Patent Literature 1: JP 2016-095542 A

SUMMARY

A first aspect according to the present invention is a compound represented by Formula (1) given below.

[Formula 1]

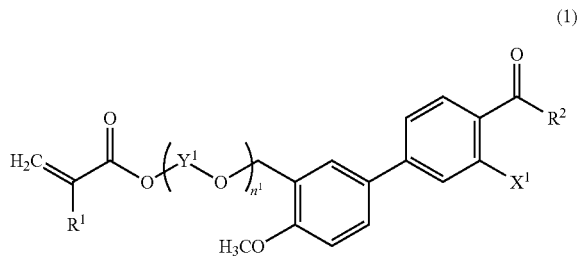

(1)

(In the formula, $R^1$ represents a hydrogen atom or a methyl group, $R^2$ represents a hydrogen atom, a phenyl group, a $C_{1\ to\ 8}$ alkyl group, or a $C_{1\ to\ 4}$ perfluoroalkyl group, $X^1$ represents a hydrogen atom or a hydroxy group, $Y^1$ represents a $C_{1\ to\ 9}$ alkylene group containing a fluorine atom or a $C_{1\ to\ 9}$ alkylene group containing no fluorine atom, and $n^1$ is an integer from 0 to 3.)

A second aspect according to the present invention is a resin precursor containing the compound described above and a curable composition.

A third aspect according to the present invention is a cured object obtained by curing the resin precursor described above.

A fourth aspect according to the present invention is an optical element using the cured object described above.

A fifth aspect according to the present invention is an optical system including the optical element described above.

A sixth aspect according to the present invention is an interchangeable camera lens including the optical system described above.

A seventh aspect according to the present invention is an optical device including the optical system described above.

An eighth aspect according to the present invention is a cemented lens including a first lens element and a second lens element joined with each other through intermediation of the cured object described above.

A ninth aspect according to the present invention is a method of manufacturing a cemented lens including a contacting step of contacting a first lens element and a second lens element with each other through intermediation of the resin precursor described above, and a joining step of joining the first lens element and the second lens element with each other by curing the resin precursor described above

DETAILED DESCRIPTION

Figure 1:
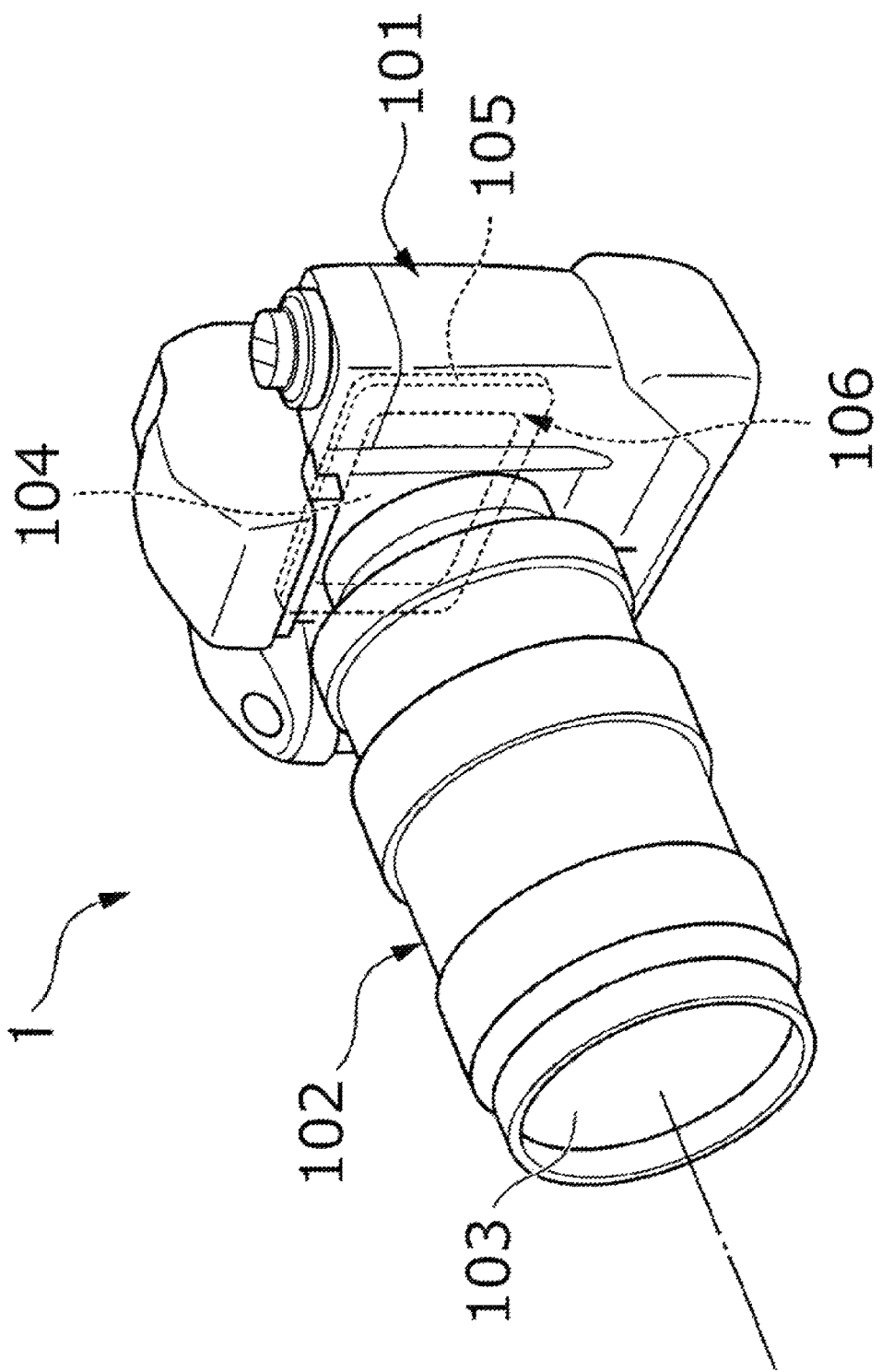
FIG. 1 is a perspective view of one example of an optical device according to the present embodiment as an imaging device.

An embodiment of the present invention (hereinafter, simply referred to as the "present embodiment") is described in detail. The present embodiment described below is an example for describing the present invention, and is not intended to limit the present invention to the contents described below. Note that, in the drawings, a positional relationship such as up, down, right, left, and the like is based on a positional relationship illustrated in the drawings, unless otherwise noted. Further, a dimensional ratio in the drawings is not intended to limit the dimensional ratio in the drawings. An acrylate and a methacrylate are collectively referred to as a "(meth)acrylate" in some cases.

A compound according to the present embodiment is a compound represented by Formula (1) given below.

[Formula 2]

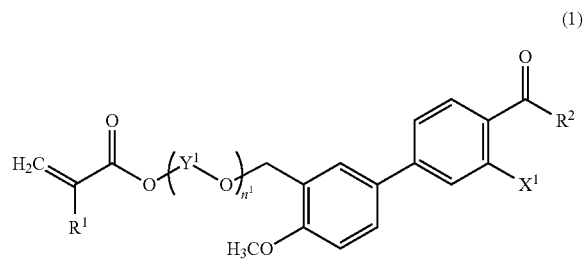

(1)

(In the formula, $R^1$ represents a hydrogen atom or a methyl group, $R^2$ represents a hydrogen atom, a phenyl group, a $C_{1\ to\ 9}$ alkyl group, or a $C_{1\ to\ 4}$ perfluoroalkyl group, $X^1$ represents a hydrogen atom or a hydroxy group, $Y^1$ represents a $C_{1\ to\ 9}$ alkylene group containing a fluorine atom or a $C_{1\ to\ 9}$ alkylene group containing no fluorine atom, and $n^1$ is an integer from 0 to 3.)

The compound represented by Formula (1) (hereinafter, referred to as the "compound (1)" in some cases) is a novel compound. The compound (1) can be used suitable as one composition of a resin precursor being a material for an optical element or the like. Further, when such compound is used, an optical element having an excellent $\theta_{g,F}$ value can be obtained. Particularly, when such compound is used as a material for a multi-layer optical element (cemented lens) obtained by combining a concave lens and a convex lens with each other, the optical element can exert an excellent optical characteristic while having a thin shape, and an excellent chromatic aberration correction effect can be provided. Note that a $\theta_{g,F}$ value is a value indicated by $(n_g-n_F)/(n_F-n_C)$ with respect to a C-line (having a wavelength of 656.3 nm), an F-line (having a wavelength of 486.1 nm), and a g-line (having a wavelength of 435.8 nm) where refractive indexes are represented by $n_C$, $n_F$, and $n_g$, respectively.

<Compound (1)>

A structure of the compound (1) is described below.

$R^1$ represents a hydrogen atom or a methyl group.

$R^2$ represents a hydrogen atom, a phenyl group, a $C_{1\ to\ 9}$ alkyl group, or a $C_{1\ to\ 4}$ perfluoroalkyl group. An alkyl group may be linear or branched. From a perspective of prevention of deposition of an insoluble component, stability, and the like at the time of preparing the resin precursor or the like, the uppermost number of carbon atoms is preferably 5, more preferably, 4. From a perspective of availability, for a perfluoroalkyl group, the uppermost number of carbon atoms is preferably 2.

Specific examples of an alkyl group for $R^2$ include an alkyl group, an ethyl group, a propyl group, an isopropyl group, an n-butyl group, an isobutyl group, a tert-butyl group, an n-pentyl group, an isopentyl group, a neopentyl group, an n-hexyl group, an isohexyl group, a neohexyl group, a heptyl group, and an octyl group. Among those, a methyl group, an ethyl group, a propyl group, an isopropyl group, an n-pentyl group, an isopentyl group, and a neopentyl group are preferred, from a perspective of prevention of deposition of an insoluble component, stability, and the like at the time of preparing the resin precursor or the like.

Specific examples of a perfluoroalkyl group for $R^2$ include a perfluoromethyl group, a perfluoroethyl group, an n-perfluoropropyl group, an isoperfluoropropyl group, an n-perfluorobutyl group, an isoperfluorobutyl group, and a tert-perfluorobutyl group. Among those, a perfluoromethyl group and a perfluoroethyl group are preferred, from a perspective of availability.

$Y^1$ represents a $C_{1\ to\ 9}$ alkylene group containing a fluorine atom or a $C_{1\ to\ 9}$ alkylene group containing no fluorine atom. An alkylene group may be linear or branched. From a perspective of prevention of deposition of an insoluble component, stability, and the like at the time of preparing the resin precursor or the like, the uppermost number of carbon atoms is preferably 6, and the lowermost number of carbon atoms is preferably 3 in a case of an alkylene group containing a fluorine atom. In a case of an alkylene group containing no fluorine atom, the uppermost number of carbon atoms is preferably 5, more preferably 4, and the lowermost number of carbon atoms is preferably 2.

Specific examples of $Y^1$ include a methylene group, an ethylene group, a propylene group, an isopropylene group, an n-butylene group, an isobutylene group, a tert-butylene group, an n-pentylene group, an isopentylene group, a neopentylene group, an n-hexylene group, an isohexylene group, a neohexylene group, a heptylene group, an octylene group, and a nonylene group. Among those, an ethylene group, a propylene group, an n-butylene group, an n-pentylene group, and a neopentylene group are preferred, from a perspective of prevention of deposition of an insoluble component, stability, and the like at the time of preparing the resin precursor or the like.

Specific examples of an alkylene group containing a fluorine atom for $Y^1$ include a 2,2-difluoro-n-propylene group, a 2,2,3,3-tetrafluoro-n-butylene group, a 2,2,3,3,4,4-hexafluoro-n-pentylene group, a 2,2,3,3,4,4,5,5-octafluoro-n-hexylene group, a 2,2,3,3,4,4,5,5,6,6-decafluoro-n-heptylene group, and a 2,2,3,3,4,4,5,5,6,6,7,7-dodecafluoro-n-octylene group. Among those, a 2,2-difluoro-n-propylene group, a 2,2,3,3-tetrafluoro-n-butylene group, a 2,2,3,3,4,4-hexafluoro-n-pentylene group, and a 2,2,3,3,4,4,5,5-octafluoro-n-hexylene group are preferred, from a perspective of stability at the time of preparing the resin precursor.

$n^1$ represents an integer from 0 to 3. From a perspective of effective prevention of deposition of an insoluble component at the time of preparing the resin precursor or the like, and availability, $n^1$ is preferably 1 or 2, more preferably, 1.

<Resin Precursor>

According to the present embodiment, a resin precursor containing the compound (1) and a curable composition can be obtained. The resin precursor can be used suitably as a resin precursor for an optical material. When used as an optical material, it is desired that the resin precursor is stable in a liquid state under an ordinary temperature and pressure. From this perspective, the resin precursor according to the present embodiment is preferably in a liquid state under an ordinary temperature and pressure. Further, when a curable composition described later is used together with the compound (1), deposition of an insoluble component can be effectively prevented, and preparation for a stable liquid-state composition can be facilitated.

The curable composition may be photocurable or thermocurable, and is preferably a photocurable composition. For example, when a large amount of a (meth)acrylate-based compound is contained, a photocurable composition is preferred.

The curable composition is not specifically limited. However, for example, one or more compound selected from a group consisting of a compound represented by Formula (2) given below, a fluorine-containing (meth)acrylate compound, a (meth)acrylate compound having a fluorene structure, and a di(meth)acrylate compound may be used. When such component is used together with the compound (1), deposition of an insoluble component can be effectively prevented, and preparation for a stable liquid composition can be facilitated. As a result, generation of deposits can be prevented during storage, and an operation of removing deposits is not required before using the composition. A uniformly cured object having a low refractive index and high dispersion can be obtained.

[Formula 3]

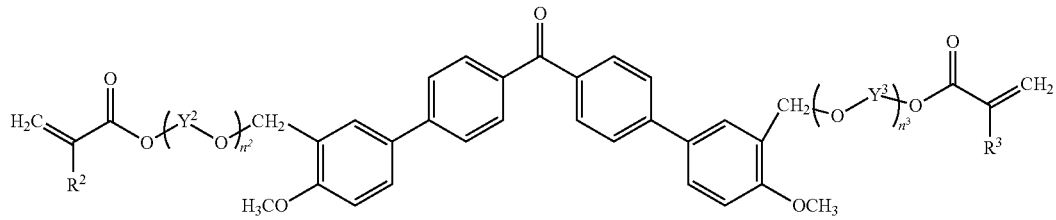

(2)

(In the formula, $R^2$ and $R^3$ independently represent a hydrogen atom or a methyl group, $Y^2$ and $Y^3$ independently represent a $C_{1 \ to \ 9}$ alkylene group, and $n^2$ and $n^3$ independently represent an integer from 0 to 3.)

The compound represented by Formula (2) (hereinafter, referred to as the "compound (2)" in some cases) is described below.

$Y^2$ and $Y^3$ independently represent a $C_{1 \ to \ 9}$ alkylene group. An alkylene group may be linear or branched. From a perspective of prevention of deposition of an insoluble component, stability, and the like at the time of preparing the resin precursor or the like, the uppermost number of carbon atoms is preferably 5, more preferably, 4. Further, the lowermost number of carbon atoms is preferably 2.

Specific examples of $Y^2$ and $Y^3$ include a methylene group, an ethylene group, a propylene group, an isopropylene group, an n-butylene group, an isobutylene group, a tert-butylene group, an n-pentylene group, an isopentylene group, a neopentylene group, an n-hexylene group, an isohexylene group, a neohexylene group, a heptylene group, an octylene group, and a nonylene group. Among those, a methylene group, an ethylene group, a propylene group, an isopropylene group, an n-pentylene group, an isopentylene group, and a neopentylene group are preferred, and an ethylene group, a propylene group, an n-butylene group, an n-pentylene group, and a neopentylene group are more preferred, from a perspective of prevention of deposition of an insoluble component, stability, and the like at the time of preparing the resin precursor or the like.

$n^2$ and $n^3$ independently represent an integer from 0 to 3. From a perspective of effective prevention of deposition of an insoluble component at the time of preparing the resin precursor or the like, and availability, $n^2$ and $n^3$ are preferably 1 or 2, more preferably, 1.

A mono-, bi-, tri-, or higher functional fluorine-containing (meth)acrylate is exemplified as a fluorine-containing (meth)acrylate compound. Among those, a bifunctional fluorine-containing (meth)acrylate is preferred from a perspective of availability. A compound represented by Formula (3) given below is exemplified as a bifunctional fluorine-containing (meth)acrylate.

(In the formula, $R^4$ and $R^5$ independently represent a hydrogen atom or a methyl group, $Y^4$ represents a $C_{2 \ to \ 12}$ perfluoroalkylene group, or —$(CF_2$—O—$CF_2)_z$—, $n^4$ and $n^5$ independently represent an integer from 1 to 12, and z represents an integer from 1 to 4.)

$R^4$ and $R^5$ independently represent a hydrogen atom or a methyl group. Among those, a hydrogen atom is preferred.

$Y^4$ represents a $C_{2 \ to \ 12}$ perfluoroalkylene group or —$(CF_2$—O—$CF_2)_z$—, and z represents an integer from 1 to 4. A perfluoroalkylene group may be linear or branched. A perfluoroalkylene group is preferably —$(CF_2)$—, —$(CF_2CF_2)$—, —$(CF_2CF_2CF_2)$—, or —$(CF_2CF_2CF_2CF_2)$—.

$n^4$ and $n^5$ independently represent an integer from 1 to 12. From a perspective of effective prevention of deposition of an insoluble component at the time of preparing the resin precursor or the like, and availability, the uppermost value of $n^4$ and $n^5$ is preferably 6, more preferably 4, further more preferably, 2.

z is preferably an integer from 1 to 3, more preferably, an integer of 1 or 2.

Specific examples of a bifunctional fluorine-containing (meth)acrylate compound include 1,4-di(meth)acryloyloxy-2,2,3,3-tetrafluorobutane, 1,6-di(meth)acryloyloxy-3,3,4,4-tetrafluorohexane, 1,6-di(meth)acryloyloxy-2,2,3,3,4,4,5,5-octafluorohexane, 1,8-di(meth)acryloyloxy-3,3,4,4,5,5,6,6-octafluorooctane, 1,8-di(meth)acryloyloxy-2,2,3,3,4,4,5,5,6,6,7,7-dodecafluorooctane, 1,9-di(meth)acryloyloxy-2,2,3,3,4,4,5,5,6,6,7,7,8,8-tetradecafluorononane, 1,10-di(meth)acryloyloxy-2,2,3,3,4,4,5,5,6,6,7,7,8,8,9,9-hexadecafluorodecane, and 1,12-di(meth)acryloyloxy-2,2,3,3,4,4,5,5,6,6,7,7,8,8,9,9,10,10,11,11-icosafluorododecane. Further, an ethylene oxide modified fluorinated bisphenol A di(meth)acrylate, a propylene oxide modified fluorinated bisphenol A di(meth)acrylate, and the like may be used as a bifunctional fluorine-containing (meth)acrylate.

Among those, a bifunctional fluorine-containing (meth)acrylate compound is preferably 1,6-di(meth)acryloyloxy-2,2,3,3,4,4,5,5-octafluorohexane, more preferably, a compound represented by Formula (3-1) given below (1,6-diacryloyloxy-2,2,3,3,4,4,5,5-octafluorohexane).

[Formula 4]

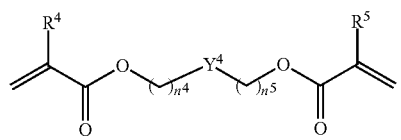

(3)

[Formula 5]

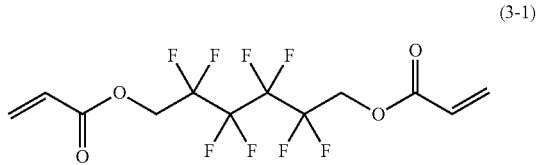

(3-1)

A content amount of a fluorine-containing (meth)acrylate compound in the resin precursor is not particularly limited. However, from a perspective of an optical characteristic such as an abbe number, compatibility with the compound (1), and the like, a total amount of a fluorine-containing (meth)acrylate compound is preferably 20 to 50 mass %, more preferably, 30 to 45 mass %, further more preferably, 35 to 42 mass %.

Examples of a (meth)acrylate compound having a fluorene structure include a monofunctional (meth)acrylate compound having a fluorene structure, a bifunctional(meth) acrylate compound having a fluorene structure, and a tri- or higher functional (meth)acrylate compound having a fluorene structure. Among those, a bifunctional(meth)acrylate compound having a fluorene structure is preferred from a perspective of availability. Specific examples of such compound include a compound represented by Formula (4) given below and a compound represented by Formula (5) given below.

[Formula 6]

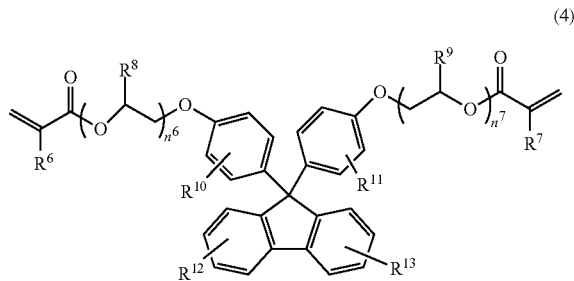

(4)

(In the formula, $R^6$ and $R^7$ independently represent a hydrogen atom or a methyl group, $R^8$ and $R^9$ independently represent a hydrogen atom, a methyl group, or an ethyl group, $R^{10}$, $R^{11}$, $R^{12}$, and $R^{13}$-independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group, and $n^6$ and $n^7$ independently represent an integer from 0 to 3.)

[Formula 7]

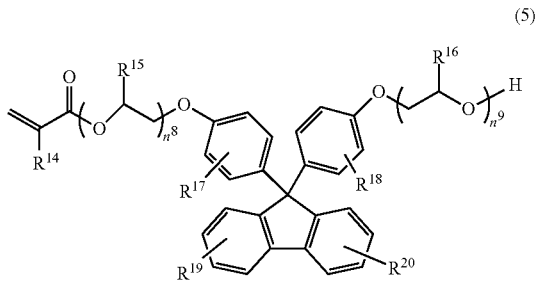

(5)

(In the formula, $R^{14}$ represents a hydrogen atom or a methyl group, $R^{15}$ and $R^{16}$ independently represent a hydrogen atom, a methyl group, or an ethyl group, $R^{17}$, $R^{18}$, $R^{19}$, and $R^{20}$ independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group, $n^8$ and $n^9$ independently represent an integer from 0 to 3.)

Formula (4) is described.

$R^6$ and $R^7$ independently represent a hydrogen atom or a methyl group. Among those, a hydrogen atom is preferred.

$R^8$ and $R^9$ independently represent a hydrogen atom, a methyl group, or an ethyl group. Among those, from a perspective of availability, a hydrogen atom is preferred.

$R^{10}$, $R^{11}$, $R^{12}$ and $R^{13}$ independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group.

As a $C_{1\ to\ 6}$ alkyl group, a linear, branched, or cyclic alkyl group may be provided. From a perspective of availability, a linear or a branched alkyl group is preferred. Specific examples of a $C_{1\ to\ 6}$ alkyl group include a methyl group, an ethyl group, a propyl group, an isopropyl group, an n-butyl group, an isobutyl group, a tert-butyl group, an n-pentyl group, an isopentyl group, a neopentyl group, an n-hexyl group, an isohexyl group, a neohexyl group, a cyclopropyl group, a cyclobutyl group, a cyclopentyl group, and a cyclohexyl group. Among those, a methyl group and an ethyl group are preferred.

A phenyl group in which a hydrogen atom may be replaced with a fluorine atom or a $C_{1\ to\ 6}$ alkyl group is obtained by replacing part or an entirety of a hydrogen atom in a phenyl group with a fluorine atom or a $C_{1\ to\ 6}$ alkyl group. As a $C_{1\ to\ 6}$ alkyl group as described above, a methyl group and an ethyl group are preferred from a perspective of availability.

$n^6$ and $n^7$ independently represent an integer from 0 to 3. Among those, $n^6$ and $n^7$ are preferably an integer from 0 to 2, more preferably, 0 or 1, further more preferably, 1, from a perspective of high hardness and transparency, and an excellent optical characteristic.

Formula (5) is described.

$R^{14}$ represents a hydrogen atom or a methyl group. Among those, a hydrogen atom is preferred.

$R^{15}$ and $R^{16}$ independently represent a hydrogen atom, a methyl group, or an ethyl group. Among those, from a perspective of availability, a hydrogen atom is preferred.

$R^{17}$, $R^{18}$, $R^{19}$ and $R^{20}$ independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group.

As a $C_{1\ to\ 6}$ alkyl group, a linear, branched, or cyclic alkyl group may be provided. From a perspective of availability, a linear or a branched alkyl group is preferred. Specific examples of a $C_{1\ to\ 6}$ alkyl group include a methyl group, an ethyl group, a propyl group, an isopropyl group, an n-butyl group, an isobutyl group, a tert-butyl group, an n-pentyl group, an isopentyl group, a neopentyl group, an n-hexyl group, an isohexyl group, a neohexyl group, a cyclopropyl group, a cyclobutyl group, a cyclopentyl group, and a cyclohexyl group. Among those, a methyl group and an ethyl group are preferred.

A phenyl group in which a hydrogen atom may be replaced with a fluorine atom or a $C_{1\ to\ 6}$ (alkyl group is obtained by replacing part or an entirety of a hydrogen atom in a phenyl group with a fluorine atom or a $C_{1\ to\ 6}$ alkyl group. As a $C_{1\ to\ 6}$ alkyl group described above, a phenyl group, a methylphenyl group, an ethylphenyl group are preferred from a perspective of availability.

$n^8$ and $n^9$ independently represent an integer from 0 to 3. Among those, $n^8$ and $n^9$ are preferably an integer from 0 to 2, more preferably, 0 or 1, further more preferably, 1, from a perspective of high hardness and transparency, and an excellent optical characteristic.

Specific examples of a (meth)acrylate compound having a fluorene structure preferably include a compound represented by Formula (4-1) given below and a compound represented by Formula (5-1) given below, more preferably, a compound (9,9-bis[4-(2-acryloyloxyethoxy)phenyl]fluorene) represented by Formula (4-1) given below.

[Formula 8]

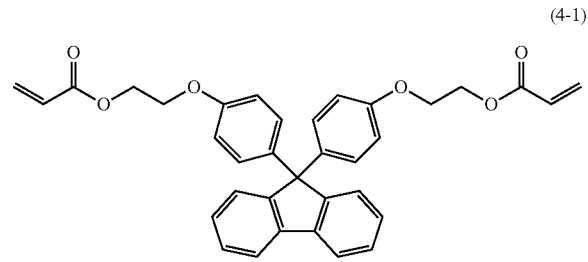

(4-1)

[Formula 9]

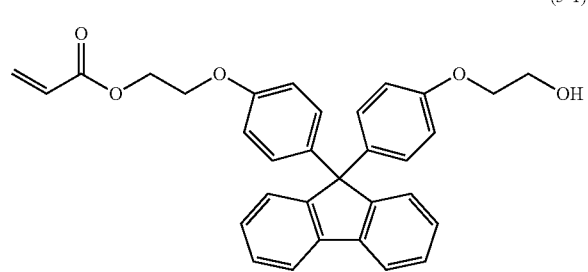

(5-1)

A content amount of a (meth)acrylate compound having a fluorene structure in the resin precursor is not particularly limited. However, from a perspective of prevention of white turbidity and prevention of deposition of an insoluble component, a total amount of a (meth)acrylate compound having a fluorene structure is preferably 20 to 50 mass %. The uppermost content amount is more preferably 40 mass %, further more preferably, 35 mass %. The lowermost content amount is more preferably 25 mass %, further more preferably, 26 mass %.

As a di(meth)acrylate compound other than each component described above, a compound having two (meth)acrylate structures is exemplified. Specific examples of a di(meth)acrylate compound include a 2-ethyl,2-butyl-propanediol (meth)acrylate, a 1,3-butyleneglycoldi(meth)acrylate, a 1,6-hexanedioldi(meth)acrylate, a 1,9-nonanediol(meth)acrylate, a 1,10-decanedioldi(meth)acrylate, a neopentylglycoldi(meth)acrylate, a dipropyleneglycoldi(meth)acrylate, a glyceroldi(meth)acrylate, an ethylene oxide modified neopentylglycoldi(meth)acrylate, a propylene oxide modified neopentylglycoldi(meth)acrylate, an ethylene oxide modified bisphenol A di(meth)acrylate, a propylene oxide modified bisphenol A di(meth)acrylate, an ethylene oxide/propylene oxide modified bisphenol A di(meth)acrylate, and a butylethylpropanedioldi(meth)acrylate.

Among those di(meth)acrylate compounds, an aliphatic di(meth)acrylate is preferred, from a perspective of compatibility with the compound (1) and the like. Among those, a 2-ethyl-2-butyl-propanediol(meth)acrylate, a 1,3-butyleneglycoldi(meth)acrylate, and a 1,6-hexanedioldi(meth)acrylate are preferred, and 1,6-hexanediol diacrylate (AHDN) is preferred more. An aliphatic di(meth)acrylate has a chemical structure that achieves high compatibility with the compound (1), and hence a stable liquid state can be maintained. As a result, the resin precursor in a liquid state, which contains the compound (1) in high concentration can be achieved. When used as an optical material, the resin precursor containing the compound (1) in high concentration can further exert an effect relating to an optical characteristic.

A content amount of a di(meth)acrylate compound in the resin precursor is not particularly limited. However, from a perspective of compatibility with the compound (1) and the like, a total amount of a di(meth)acrylate compound is preferably 10 to 80 mass %. The uppermost content amount is more preferably 60 mass %, further more preferably, 50 mass %. The lowermost content amount is more preferably 20 mass %, further more preferably, 35 mass %.

The curable composition according to the present embodiment may contain a component other than those described above. A monofunctional (meth)acrylate, a trifunctional (meth)acrylate, and a tetrafunctional (meth)acrylate are exemplified. By using those together, hardness, transparency, and an optical characteristic of the resin can be adjusted. Among those, a monofunctional (meth)acrylate is preferred, from a perspective of improving compatibility with the compound (1).

Examples of a monofunctional (meth)acrylate include a methyl(meth)acrylate, ethyl(meth)acrylate, a butyl(meth)acrylate, an isodecyl(meth)acrylate, a lauryl(meth)acrylate, a tridecyl(meth)acrylate, an acetyl(meth)acrylate, a stearyl (meth)acrylate, a tert-butyl(meth)acrylate, a 2-ethylhexyl (meth)acrylate, a 2-hydroxybutyl(meth)acrylate, a 2-hydroxyethyl(meth)acrylate, a 2-hydroxypropyl(meth)acrylate, a 3-methoxybutyl(meth)acrylate, a diethylaminoethyl(meth)acrylate, a phenoxypolyethyleneglycol(meth)acrylate, an isostearyl(meth)acrylate, a paracumylphenoxyethyleneglycol(meth)acrylate, a dimethylaminoethyl(meth)acrylate, a 2-ethylhexylcarbitol(meth)acrylate, a butoxyethyl(meth)acrylate, an ethoxydiethyleneglycol(meth)acrylate, a lauroxypolyethyleneglycol (meth)acrylate, a polyethyleneglycol(meth)acrylate, a methoxydipropyleneglycolacrylate, a methoxytrypropyleneglycolacrylate, an ethoxydipropyleneglycolacrylate, an ethoxytrypropyleneglycolacrylate, a polypropyleneglycol (meth)acrylate, an acryloxypolyethyleneglycol(meth)acrylate, a stearoxypolyethyleneglycol(meth)acrylate, an octoxypolyethyleneglycol-polypropyleneglycol(meth)acrylate, a poly(propyleneglycol-tetramethyleneglycol) (meth) acrylate, a poly(ethyleneglycol-tetramethyleneglycol) (meth)acrylate, a methoxypolyethyleneglycol(meth)acrylate, a methoxypolypropyleneglycol(meth)acrylate, and a benzil(meth)acrylate. Among those, methoxytrypropyleneglycolacrylate and ethoxytrypropyleneglycolacrylate are preferred, from a perspective of a structure regarding compatibility with the compound (1) and the like.

Examples of a trifunctional(meth)acrylate includes a tris (acryloxyethyl)isocyanurate, a tris(methacryloxyethyl) isocyanurate, an epichlorohydrin modified glyceroltri(meth)acrylate, an ethylene oxide modified glyceroltri(meth)acrylate, a propylene oxide modified glyceroltri(meth)acrylate, a caprolactone modified trimethylolpropanetri (meth)acrylate, an ethylene oxide modified trimethylolpropanetri(meth)acrylate, a propylene oxide modified trimethylolpropanetri(meth)acrylate, a pentaerythritoltri(meth)acrylate, and a trimethylolpropanetri(meth)acrylate. Among those, a pentaerythritoltri(meth)acrylate is preferred, from a perspective of a structure regarding compatibility with the compound (1) and the like.

As a tetrafunctional (meth)acrylate, a pentaerythritol tetra (meth)acrylate, a dipentaerythritol hydroxypenta(meth)acrylate, and a ditrimethylolpropane tetra(meth)acrylate are exemplified. Among those, a dipentaerythritol hydroxypenta (meth)acrylate is preferred, from a perspective of a structure regarding compatibility with the compound (1) and the like.

When the resin precursor according to the present embodiment is photocurable, the resin precursor may further contain a photopolymerization initiator. The photopolymerization initiator is not particularly limited as long as polymerization of monomeric components can be initiated with light irradiation, and a publicly-known photopolymerization initiator used for photo-curing a resin may be used. Light used for light irradiation may be selected as appropriate in accordance with a photopolymerization initiator to be used, and visible light, ultraviolet light, an electron beam, and the like are generally used.

A content amount of the photopolymerization initiator depends on a type of used components or a type of irradiation light, and, in general, is preferably 0.1 to 5 mass %.

As the photopolymerization initiator, for example, a phosphine-based or acetophenone-based photopolymerization initiator is preferred, from a perspective of reactivity. As a phosphine-based photopolymerization initiator, a bis(2-4-6-trimethylbenzoyl)-phenylphosphineoxide, a 2,4,6-trimethylbenzoyl-diphenyl-phosphineoxide, and the like are preferred. As an acetophenone-based photopolymerization initiator, alkylphenyl ketones having a hydroxyl group at the alpha-position are preferred, and a 1-hydroxy-cyclohexyl-phenyl-ketone, a 2-hydroxy-2-methyl-1-phenyl-propane-1-one, and the like are more preferred, from a perspective of prevention of yellowing of a resin in addition to a perspective of reactivity.

The resin precursor according to the present embodiment may further contain a photostabilizer. A publicly-known photostabilizer may be used as the photostabilizer. Suitable examples of the photostabilizer include a hindered amine based material such as a bis(2,2,6,6-tetramethyl-4-piperidyl)sebacate, a bis(1,2,2,6,6-pentamethyl-4-piperidyl)sebacate, and a methyl-1,2,2,6,6-pentamethyl-4-piperidylsebacate.

The resin precursor according to the present embodiment may further contain a polymerization-inhibitor. A publicly-known polymerization-inhibitor may be used as the polymerization-inhibitor. Suitable examples of the polymerization-inhibitor include hydroquinones such as a p-benzoquinone, a hydroquinone, a hydroquinonemonomethylether, and a 2,5-diphenylparabenzoquinone, substituted catechols such as a T-butyl catechol, a phenothiazine, amines such as a diphenylamine, N-oxy radicals such as a tetramethylpiperidinyl-N-oxy radical (TEMPO), a nitrosobenzene, a picric acid, molecular oxygen, and sulfur. Among those, hydroquinones, a phenothiazine, and N-oxy radicals are more preferred, from a perspective of versatility and prevention of polymerization.

The resin precursor according to the present embodiment may further contain an ultraviolet light absorber. A publicly-known ultraviolet light absorber may be used as the ultraviolet light absorber. Suitable examples include a 2-(2-hydroxy-5-t-octylphenyl)-2H-benzotriazole. When used together with the photostabilizer, the ultraviolet light absorber can be expected to exert a further excellent effect.

As suitable combinations of the components described above for the curable composition that is used together with the compound (1), the curable composition preferably contain a fluorine-containing (meth)acrylate compound or a (meth)acrylate compound having a fluorene structure, and a di(meth)acrylate compound, more preferably, a fluorine-containing (meth)acrylate compound and a di(meth)acrylate compound, further more preferably, an aliphatic fluorine-containing (meth)acrylate compound and an aliphatic di(meth)acrylate compound.

As a specific component combination of the suitable combinations described above, the curable composition preferably contains any one selected from a group consisting of a 9,9-bis[4-(2-acryloyloxyethoxy)phenyl]fluorene, a methoxytrypropyleneglycolacrylate, a 1,6-di(meth)acryloyloxy-2,2,3,3,4,4,5,5-octafluorohexane, a 1-hydroxy-cyclohexyl-phenyl-ketone, a bis(2-4-6-trimethylbenzoyl)-phenylphosphineoxide, a bis(1,2,2,6,6-pentamethyl-4-piperidyl)sebacate, a methyl 1,2,2,6,6-pentamethyl-4-piperidylsebacate, a 2-(2-hydroxy-5-t-octylphenyl)-2H-benzotriazole, and a 1,6-hexanediol diacrylate.

Among those, it is more preferred that at least any one selected from a group consisting of a 1,6-di(meth)acryloyloxy-2,2,3,3,4,4,5,5-octafluorohexane, a 9,9-bis[4-(2-acryloyloxyethoxy)phenyl]fluorene, and a 1,6-hexanediol diacrylate be contained, from a perspective of effective prevention of deposition of an insoluble component and easy preparation for a stable liquid-state composition. Further, it is further more preferred that two or more kinds selected from a group consisting of a 1,6-di(meth)acryloyloxy-2,2,3,3,4,4,5,5-octafluorohexane, a 9,9-bis[4-(2-acryloyloxyethoxy)phenyl]fluorene, and a 1,6-hexanediol diacrylate be contained. Further, it is further more preferred that a 1,6-di(meth)acryloyloxy-2,2,3,3,4,4,5,5-octafluorohexane, a 9,9-bis[4-(2-acryloyloxyethoxy)phenyl]fluorene, and a 1,6-hexanediol diacrylate be contained. When such component is used together with the compound (1), preparation is further facilitated to obtain a liquid-state composition having high stability under an ordinary temperature.

In addition to the combination of the curable composition described above, it is preferred that the compound (2) be also used together. With this, an achievable range of an optical characteristic is broadened, and a degree of design freedom for a product using the compound can be improved.

A content amount of the compound (1) in the resin precursor is not particularly limited. However, from a perspective of maintaining high stability in a liquid state, the content amount is preferably 10 to 50 mass %. From the perspective described above, the uppermost content amount is more preferably 30 mass %, further more preferably, 25 mass %. The lowermost content amount is more preferably 15 mass %.

<Cured Object>

A cured object can be obtained by curing the resin precursor according to the present embodiment. A curing method may be photocuring or thermal curing, depending on a property of the contained curable composition. As the curing method, for example, a method of using an ultraviolet-light curable composition and performing irradiation of ultraviolet light may be employed.

As a physical property of the cured object, a $\theta_{g,F}$ value is preferably 0.5 or greater, more preferably, 0.6 or greater, further more preferably, 0.7 or greater. An abbe number $(v_d)$ is preferably 10 or greater and 40 or less. Further, it is preferred that both the $\theta_{g,F}$ value and the abbe number $(v_d)$ respectively satisfy the numerical ranges described above. A refractive index $(n_d)$ with respect to a d-line may be 1.50 or greater and 1.65 or less.

A glass material and an optical material formed of an organic resin or the like have a tendency of reducing a refractive index as approaching a small wavelength side. As an index indicating a wavelength dispersion characteristic of a refractive index, the $\theta_{g,F}$ value and the abbe number $(v_d)$ are used. These values are unique to optical materials. In a refraction optical system, reduction in chromatic aberration has been attempted by appropriately combining optical materials having different dispersion characteristics. However, when the configuration or the number of lenses is limited from a perspective of design requirement or the like, it is difficult to correct chromatic aberration sufficiently in some cases. In view of this, the cured object according to the present embodiment has a high $\theta_{g,F}$ value, and has a unique dispersion characteristic. The cured object according to the present embodiment has such property, and hence has an excellent chromatic aberration correction function. Thus, such problem can be solved.

Further, an inner transmittance of the cured object is preferably 80% or greater over a wavelength range from 400 nm to 450 nm. According to the present embodiment, the cured object having a high inner transmittance can be obtained as an optical material.

<Optical Element, Optical System, Interchangeable Camera Lens, Optical Device, and the Like>

The cured object according to the present embodiment may be used as an optical element. The optical element including the cured object includes a mirror, a lens, a prism, and a filter. Suitable usage examples include an optical lens. Further, the optical element according to the present embodiment may be used for an optical system including the optical element.

The optical system according to the present embodiment may be used for an interchangeable camera lens including the optical system. Publicly-known configurations may be employed for the optical element, the optical lens, and the interchangeable camera lens. Further, the optical system according to the present embodiment may be used for an optical device including the optical system. The optical device including the optical system is not particularly limited, and examples thereof include an imaging device such as a lens-interchangeable camera and a fixed lens camera, and an optical microscope.

(Imaging Device)

FIG. 1 is a perspective view of one example of an optical device according to the present embodiment as an imaging device.

An imaging device 1 is a so-called digital single-lens reflex camera (a lens-interchangeable camera), and a photographing lens (an optical system) 103 includes the cured object according to the present embodiment. A lens barrel 102 is mounted to a lens mount (not illustrated) of a camera body 101 in a removable manner. Further, an image is formed with light, which passes through the lens 103 of the lens barrel 102, on a sensor chip (solid-state imaging elements) 104 of a multi-chip module 106 arranged on a back surface side of the camera body 101. The sensor chip 104 is a so-called bare chip such as a CMOS image sensor, and the multi-chip module 106 is, for example, a Chip On Glass (COG) type module including the sensor chip 104 being a bare chip mounted on a glass substrate 105.

Figure 2:
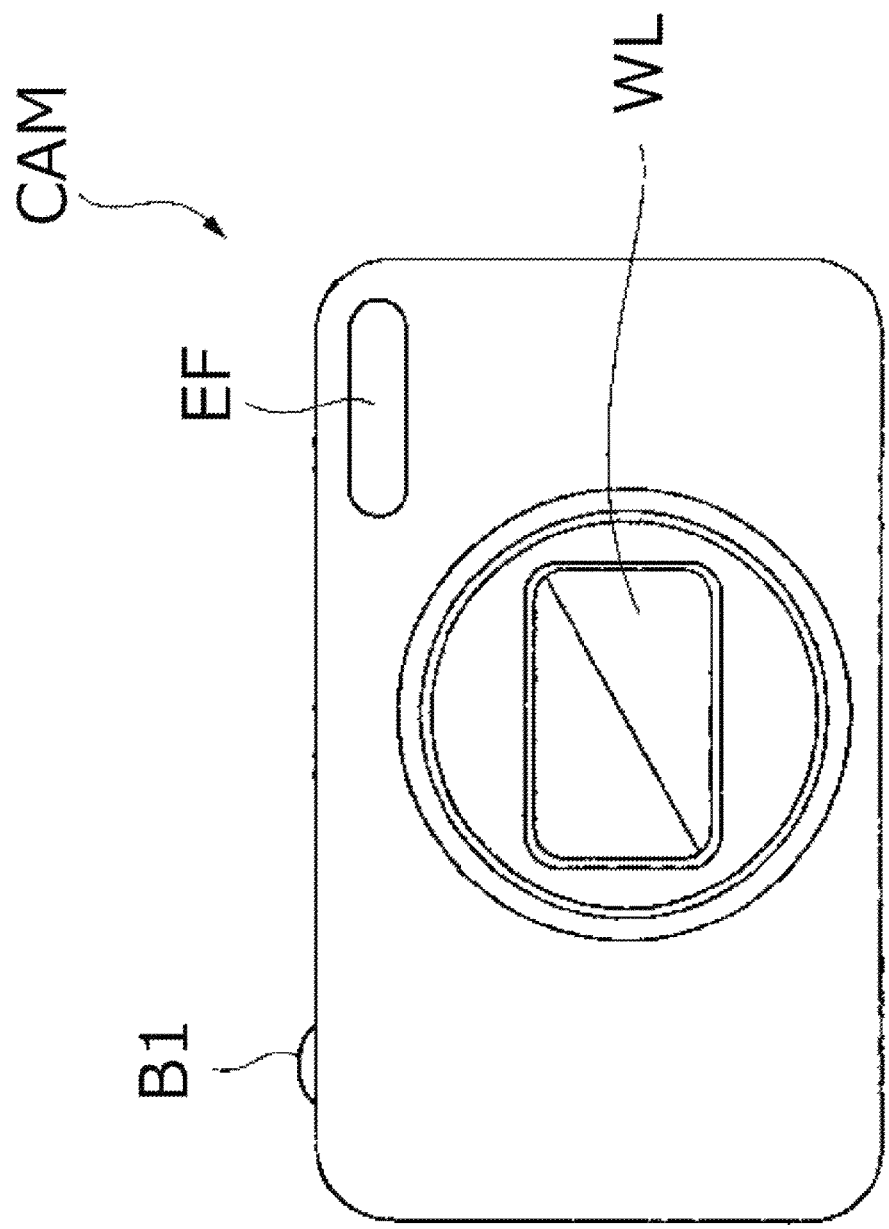
FIG. 2 is a front view of another example of the optical device according to the present embodiment as an imaging device.
Figure 3:
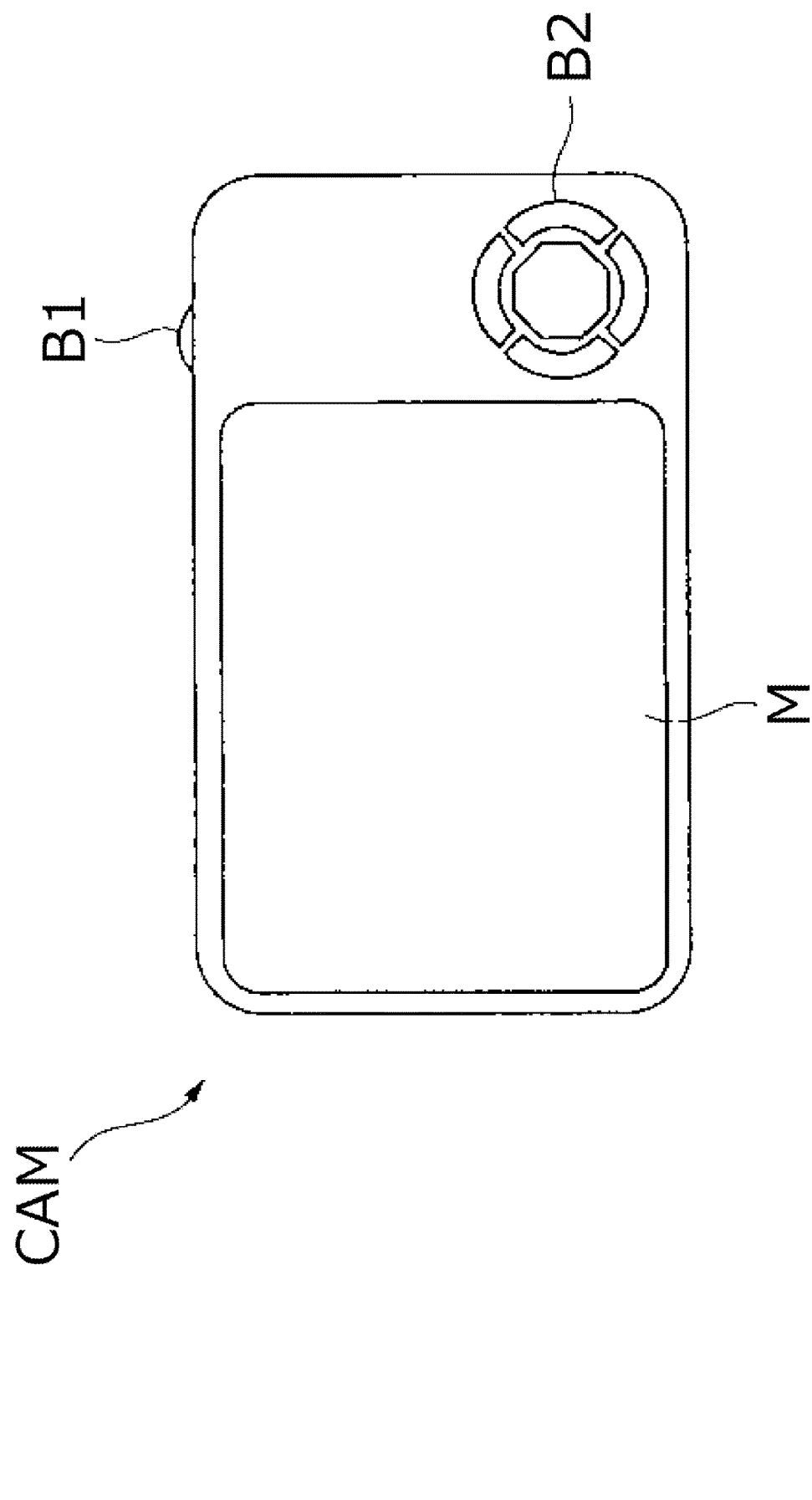
FIG. 3 is a back view of the imaging device of FIG. 2.

FIG. 2 is a front view of another example of the optical device according to the present embodiment as an imaging device. FIG. 3 is a back view of the imaging device.

The imaging device CAM is a so-called digital still camera (a fixed lens camera), and a photographing lens (an optical system) WL includes the cured object according to the present embodiment. When a power button (not illustrated) of the imaging device CAM is pressed, a shutter (not illustrated) of the photographing lens WL is opened, light from an object to be imaged (a body) is converged by the photographing lens WL and forms an image on imaging elements arranged on an image surface. An object image formed on the imaging elements is displayed on a liquid crystal monitor M arranged on the back of the imaging device CAM. A photographer decides composition of the object image while viewing the liquid crystal monitor M, then presses down a release button B1, and captures the object image on the imaging elements. The object image is recorded and stored in a memory (not illustrated). An auxiliary light emitting unit EF that emits auxiliary light in a case that the object is dark and a function button B2 to be used for setting various conditions of the imaging device CAM and the like are arranged on the imaging device CAM.

A higher resolution, lighter weight, and a smaller size are demanded for the optical system to be used in such digital camera or the like. In order to achieve such demands, it is effective to use optical glass with a high refractive index as the optical system. From such viewpoint, the optical glass according to the present embodiment is suitable as a member of such optical device. Note that, in addition to the imaging device described above, examples of the optical device to which the present embodiment is applicable include a projector and the like. In addition to the lens, examples of the optical element include a prism and the like.

(Multi-Photon Microscope)

Figure 4:
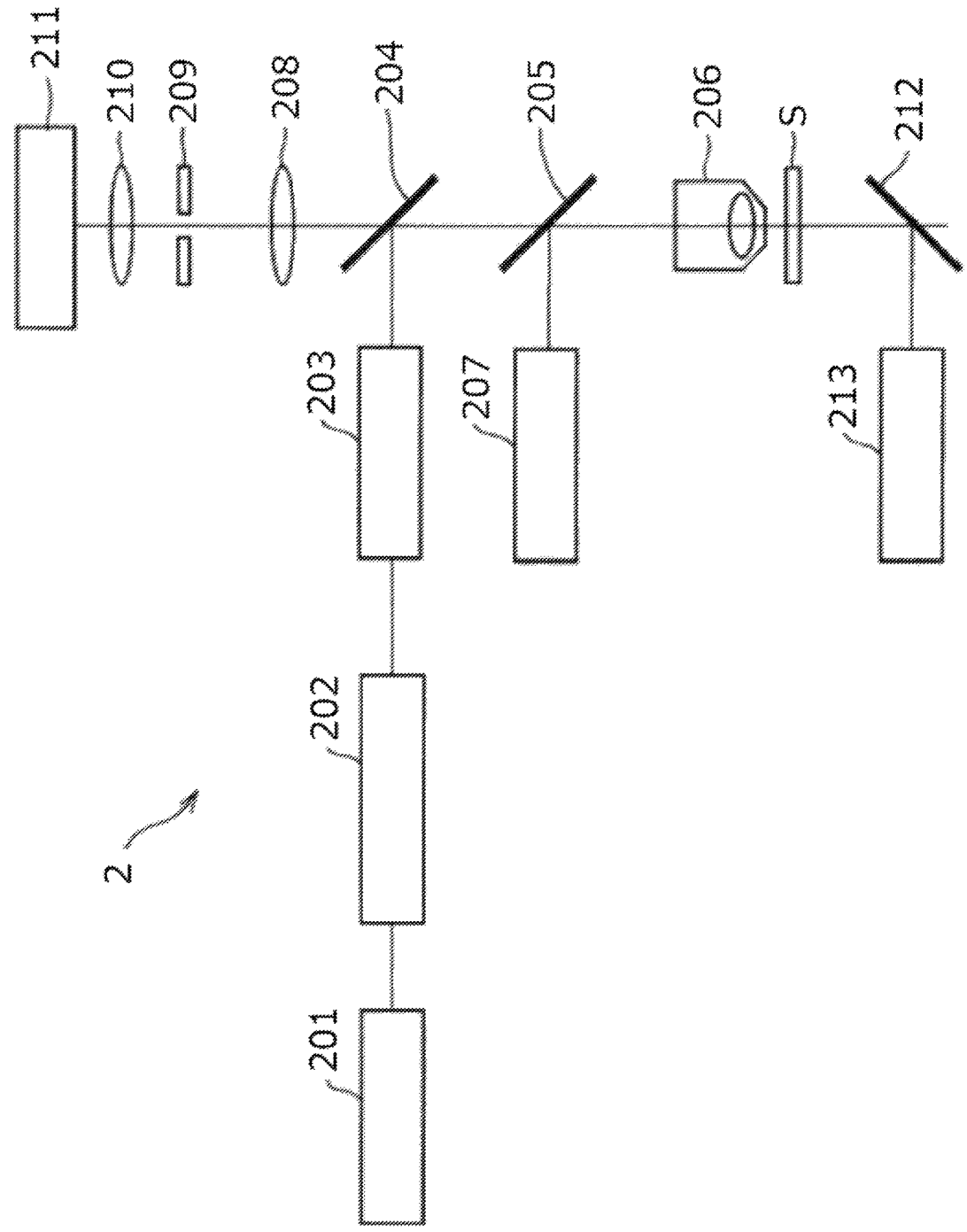
FIG. 4 is a block diagram illustrating one example of the optical device according to the present embodiment as a multi-photon microscope.

FIG. 4 is a block diagram illustrating one example of the optical device according to the present embodiment as a multi-photon microscope.

The multi-photon microscope 2 includes an objective lens 206, a condensing lens 208, and an image forming lens 210, as optical elements. Hereinafter, description is mainly made on the optical system of the multi-photon microscope 2.

A pulse laser device 201 emits ultrashort pulse light having, for example, a near infrared wavelength (approximately 1,000 nm) and a pulse width of a femtosecond unit (for example, 100 femtoseconds). In general, ultrashort pulse light immediately after being emitted from the pulse laser device 201 is linearly polarized light that is polarized in a predetermined direction.

A pulse division device 202 divides the ultrashort pulse light, increases a repetition frequency of the ultrashort pulse light, and emits the ultrashort pulse light.

A beam adjustment unit 203 has a function of adjusting a beam diameter of the ultrashort pulse light, which enters from the pulse division device 202, to a pupil diameter of the objective lens 206, a function of adjusting convergence and divergence angles of the ultrashort pulse light in order to correct chromatic aberration (a focus difference) on an axis of a wavelength of multi-photon excitation light emitted from a sample S and the wavelength of the ultrashort pulse light, a pre-chirp function (group velocity dispersion compensation function) providing inverse group velocity dispersion to the ultrashort pulse light in order to correct the pulse width of the ultrashort pulse light, which is increased due to group velocity dispersion at the time of passing through the optical system, and the like.

The ultrashort pulse light emitted from the pulse laser device 201 have a repetition frequency increased by the pulse division device 202, and is subjected to the above-mentioned adjustments by the beam adjustment unit 203. Furthermore, the ultrashort pulse light emitted from the beam adjustment unit 203 is reflected on a dichroic mirror 204 in a direction toward a dichroic mirror 205, passes through the dichroic mirror 205, is converged by the objective lens 206, and is radiated to the sample S. At this time, an observation surface of the sample S may be scanned with the ultrashort pulse light through use of scanning means (not illustrated).

For example, when the sample S is subjected to fluorescence observation, a fluorescent pigment by which the sample S is dyed is subjected to multi-photon excitation in an irradiated region with the ultrashort pulse light and the vicinity thereof on the sample S, and fluorescence having a wavelength shorter than a near infrared wavelength of the ultrashort pulse light (hereinafter, also referred to "observation light") is emitted.

The observation light emitted from the sample S in a direction toward the objective lens 206 is collimated by the objective lens 206, and is reflected on the dichroic mirror 205 or passes through the dichroic mirror 205 depending on the wavelength.

The observation light reflected on the dichroic mirror 205 enters a fluorescence detection unit 207. For example, the fluorescence detection unit 207 is formed of a barrier filter, a photo multiplier tube (PMT), or the like, receives the observation light reflected on the dichroic mirror 205, and outputs an electronic signal depending on an amount of the light. The fluorescence detection unit 207 detects the observation light over the observation surface of the sample S, in conformity with the ultrashort pulse light scanning on the observation surface of the sample S.

Meanwhile, the observation light passing through the dichroic mirror 205 is de-scanned by scanning means (not illustrated), passes through the dichroic mirror 204, is converged by the condensing lens 208, passes through a pinhole 209 provided at a position substantially conjugate to a focal position of the objective lens 206, passes through the image forming lens 210, and enters a fluorescence detection unit 211.

For example, the fluorescence detection unit 211 is formed of a barrier filter, a PMT, or the like, receives the observation light forming an image on a light receiving surface of the fluorescence detection unit 211 by the image forming lens 210, and outputs an electronic signal depending on an amount of the light. The fluorescence detection unit 211 detects the observation light over the observation surface of the sample S, in conformity with the ultrashort pulse light scanning on the observation surface of the sample S.

Note that, all the observation light emitted from the sample S in a direction toward the objective lens 206 may be detected by the fluorescence detection unit 211 by excluding the dichroic mirror 205 from the optical path.

The observation light emitted from the sample S in a direction opposite to the objective lens 206 is reflected on a dichroic mirror 212, and enters a fluorescence detection unit 213. The fluorescence detection unit 213 is formed of, for example, a barrier filter, a PMT, or the like, receives the observation light reflected on the dichroic mirror 212, and outputs an electronic signal depending on an amount of the light. The fluorescence detection unit 213 detects the observation light over the observation surface of the sample S, in conformity with the ultrashort pulse light scanning on the observation surface of the sample S.

The electronic signals output from the fluorescence detection units 207, 211, and 213 are input to, for example, a computer (not illustrated). The computer is capable of generating an observation image, displaying the generated observation image, storing data on the observation image, based on the input electronic signals.

<Cemented Lens and Method for Manufacturing Cemented Lens>

A case where the compound, the resin precursor, and the cured object according to the present embodiment are used for a single lens is mainly described above. The compound, the resin precursor, the cured object and the like according to the present embodiment may be suitably used as a joining member of a cemented lens including a plurality of lenses.

Figure 5:
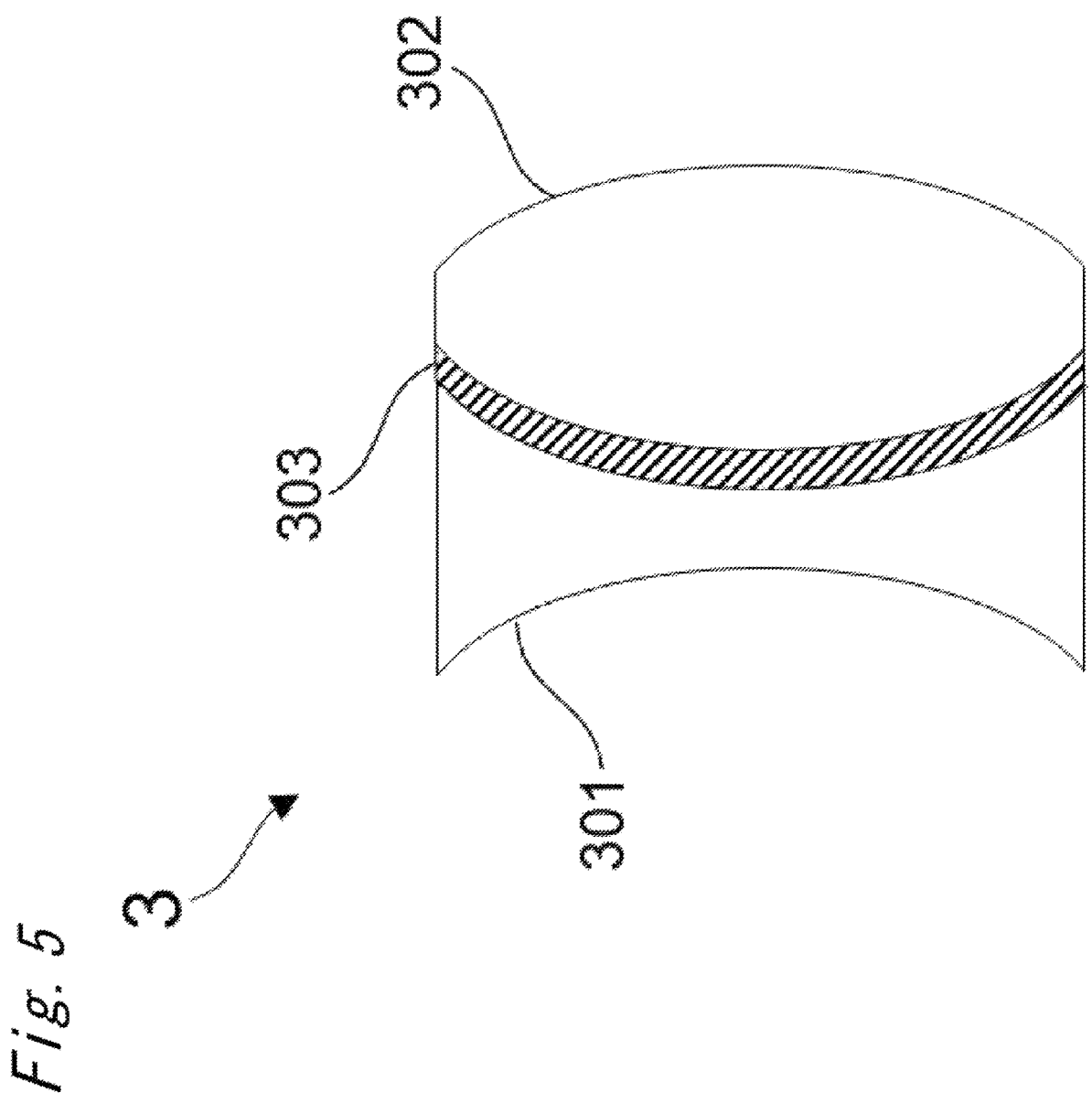
FIG. 5 is a schematic view illustrating one example of a cemented lens according to the present embodiment.

FIG. 5 is a schematic view illustrating one example of the cemented lens according to the present embodiment.

A cemented lens includes a first lens element 301 and a second lens element 302 joined with each other through intermediation of the cured object 303 according to the present embodiment. Note that, the lenses forming the cemented lens are referred to as "lens elements" as described above in some cases from a viewpoint of clearly stating that the lenses are the elements of the cemented lens. In this manner, the cured object 303 according to the present embodiment can be caused to function as the joining member described above.

When the compound, the resin precursor, and the cured object according to the present embodiment are used for a cemented lens including two lens elements, there is exemplified a manufacturing method including, firstly, (1) a contacting step of contacting the first lens element and the second lens element with each other through intermediation of the resin precursor according to the present embodiment, and (2) a joining step of curing the resin precursor and joining the first lens element and the second lens element with each other.

(1) In the contacting step, the resin precursor according to the present embodiment is interposed in a pre-cured state between the first lens element and the second lens element. For example, when the resin precursor is a liquid-state composition, the resin precursor is applied on contact surfaces between the first lens element and the second lens element, and both the lens elements are laid over with each other.

(2) In the joining step, a method of curing the resin precursor may be photocuring or thermal curing. Curing is performed preferably by irradiating the resin precursor with light. The resin precursor is preferably irradiated with light through the first lens element or the second lens element. The compound, the resin precursor, and the cured object according to the present embodiment can prevent yellowing due to aging, and can maintain high transparency for a long period of time. From this perspective, the manufacturing method is suitable.

The cementing lens thus obtained may be used for an optical system, similarly as described with the single lens. The cemented lens according to the present embodiment may be used for an optical device including an interchangeable camera lens and an optical system, similarly as described with the single lens. Note that, in the aspect described above, description is made on the cemented lens using the two lens elements. The present invention is however not limited thereto, and a cemented lens using three or more lens elements may be used. When a cemented lens using three or more lens elements is obtained, the cured object according to the present embodiment may be applied to all the joining members between each of the lens elements. However, the present invention is not limited thereto, and the cured object according to the present embodiment is only required to be applied to at least one of the joining members.

EXAMPLES

The present invention is further described in detail with Examples and Comparative Examples given below. However, the following examples are not intended to limit the present invention at all. First, compounds were synthesized, resin precursors containing those compounds and cured objects obtained therefrom were produced, and physical property evaluation was performed on each resultant.

I. Production of Compound and Physical Property Evaluation

Example 1 (Synthesis of Compound (1A))

(Synthesis of Intermediate Compound (a1))

10.00 g (46.1 mmol) of 2-methoxy-5-bromobenzylalcohol and 200 mL of toluene (dehydration) were measured and put in a 500 milliliter-reactor vessel. The resultant was stirred to obtain a uniform solution, and was cooled to a temperature of 0 degrees Celsius. 6.24 g (23.0 mmol) of phosphorus tribromide (PBr$_3$) were slowly dropped to the resultant. After stirring at a room temperature for three hours, the reaction solution was checked with thin layer chromatography (TLC), and disappearance of 2-methoxy-5-bromobenzylalcohol was confirmed. Subsequently, 200 mL of pure water was added to the reaction solution, and the resultant was stirred again for 30 minutes. The resultant was separated into an organic layer and a water layer by a separating funnel, and then the water layer was extracted twice by 25 mL of toluene. The organic layer and the extracted layer were collectively washed twice with 100 mL of a saturated saline solution, were replaced in a vessel, and anhydrous magnesium sulfate was added.

Solid matters were removed through filtration, and the filtrate was concentrated under a low pressure at a temperature of 70 degrees Celsius. The obtained slightly orange-colored liquid was dried under a low pressure at a temperature of 70 degrees Celsius for four hours, and thus an intermediate compound (a1) was obtained. The yield amount was 11.82 g (42.2 mmol), and the yield was 91.6%.

[Formula 10]

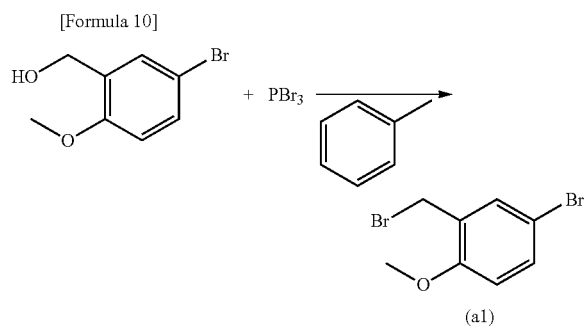

(Synthesis of Intermediate Compound (a2))

2.53 g (63.3 mmol) of sodium hydride (NaH; concentration of 60%) and 150 mL of tetrahydrofuran (dehydration) were measured and put in a 500 milliliter-reactor vessel, and the resultant was cooled to a temperature of 0 degree Celsius. A dilute solution of 13.19 g (126.7 mmol) of 2,2-dimethyl-1,3-propanediol with 30 mL of tetrahydrofuran were slowly dropped to the resultant. After stirring at a room temperature for an hour, a dilute solution of 11.82 g (42.2 mmol) of the intermediate compound (a1) with 20 mL of tetrahydrofuran was added rapidly. After stirring at a temperature of 60 degrees Celsius for five hours, the reaction solution was checked with TLC, and disappearance of the intermediate compound (a1) was confirmed. Subsequently, 200 mL of 2N hydrochloric acid were added to the reaction solution. The resultant was separated into an organic layer and a water layer by a separating funnel, and then the water layer was extracted twice by 50 mL of ethyl acetate. The organic layer and the extracted layer were collectively washed twice with 100 mL of a saturated saline solution, were replaced in a vessel, and anhydrous magnesium sulfate was added.

Solid matters were removed through filtration, and the filtrate was concentrated under a low pressure at a temperature of 50 degrees Celsius. The slightly yellow-colored liquid obtained through refining with a silica gel column (a development solvent satisfied n-hexane:ethyl acetate=3:1) was dried under a low pressure at a temperature of 70 degrees Celsius for four hours, and thus an intermediate compound (a2) was obtained. The yield amount was 11.02 g (36.3 mmol), and the yield was 86.1%.

[Formula 11]

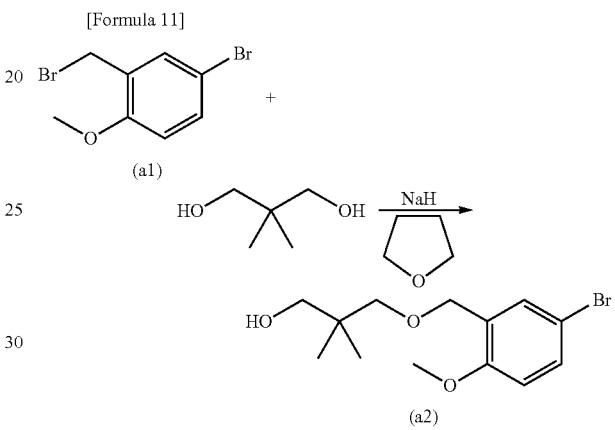

(Synthesis of Intermediate Compound (a3))

10.55 g (34.8 mmol) of the intermediate compound (a2), 7.42 g (45.2 mmol) of 4-acetylphenylboronic acid, and 140 mL of dioxane were measured and put in a 500 milliliter-reactor vessel. A uniform solution was not obtained even after stirring. A dilute solution of 14.38 g (135.7 mmol) of sodium hydrogen carbonate with 70 mL of pure water and 804 mg (0.696 mmol) of a tetrakis(triphenylphosphine) palladium(0) complex were added to the resultant. While water at a temperature of 5 degrees Celsius was caused to flow through a cooling tube, the resultant was stirred at a temperature of 110 degrees Celsius for four hours. After that, the reaction solution was checked with TLC, and disappearance of the intermediate compound (a2) was confirmed. At this point, 90 mL of a 2N ammonium chloride aqueous solution were added to the reaction solution. The resultant was separated into an organic layer and a water layer by a separating funnel, and then the water layer was extracted twice by 30 mL of ethyl acetate. The organic layer and the extracted layer were collectively washed twice with 100 mL of a saturated saline solution, were replaced in a vessel, and anhydrous magnesium sulfate was added.

Solid matters were removed through filtration, and the filtrate was concentrated under a low pressure at a temperature of 50 degrees Celsius. The slightly yellow-colored liquid obtained through refining with a silica gel column (a development solvent satisfied n-hexane:ethyl acetate=2:1) was dried under a low pressure at a temperature of 70 degrees Celsius for four hours, and thus an intermediate compound (a3) was obtained. The yield amount was 9.36 g (27.3 mmol), and the yield was 78.6%.

[Formula 12]

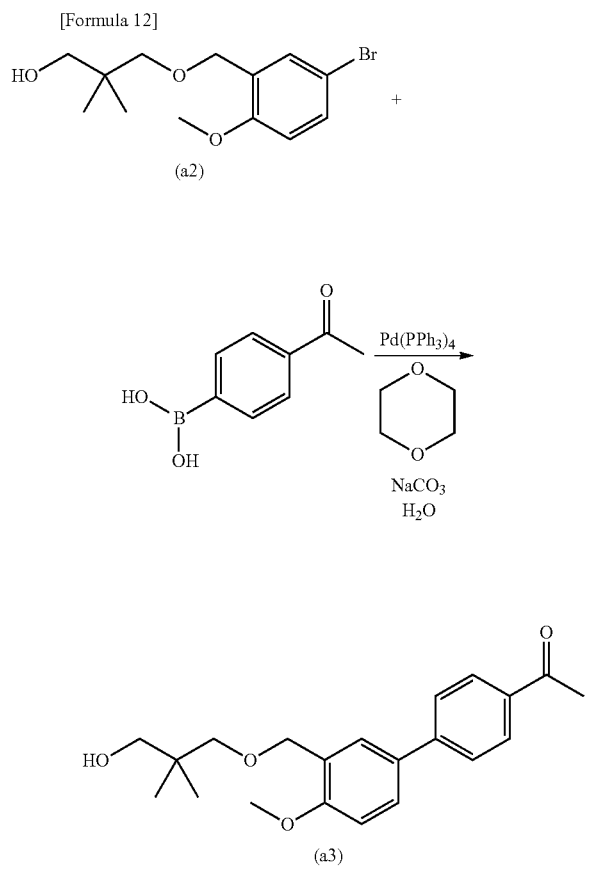

(a2)

[Formula 13]

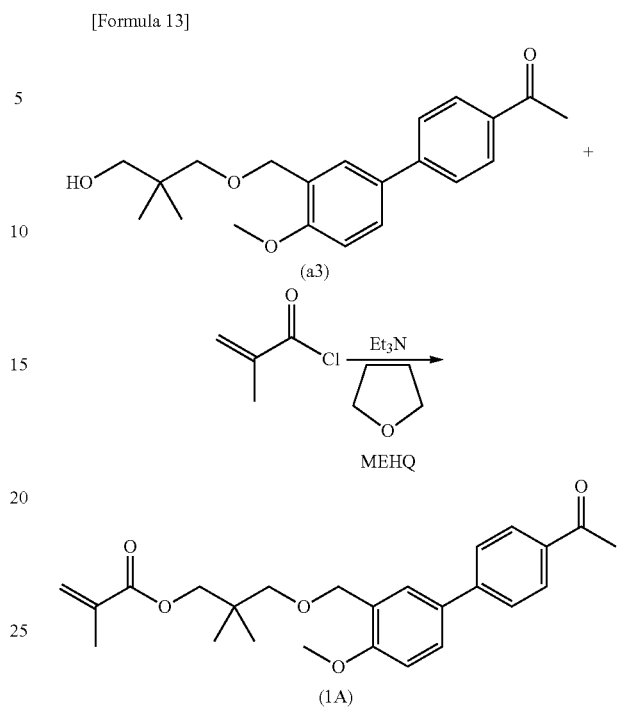

(Synthesis of Target Compound (1A))

7.57 g (22.1 mmol) of the intermediate compound (a3), 5.59 g (55.3 mmol) of triethylamine (Et$_3$N), 151 mg (1.22 mmol) of 4-methoxyphenol (MEHQ), and 70 mL of tetrahydrofuran (dehydration) were measured and put in a 200 milliliter-reactor vessel. The resultant was stirred to obtain a uniform solution, and was cooled to a temperature of 0 degrees Celsius. 4.62 g (44.2 mmol) of methacryloyl chloride were slowly dropped to the resultant. Stirring was sequentially performed for two hours. After that, the reaction solution was checked with TLC, and substantial disappearance of the intermediate compound (a3) was confirmed. At this point, 70 mL of a 2N sodium hydroxide aqueous solution were added to the reaction solution. The resultant was separated into an organic layer and a water layer by a separating funnel, and then the water layer was extracted twice by 20 mL of ethyl acetate. The organic layer and the extracted layer were collectively washed twice with 100 mL of a saturated saline solution, were replaced in a vessel, and anhydrous magnesium sulfate was added.

Solid matters were removed through filtration, and the filtrate was concentrated under a low pressure at a temperature of 40 degrees Celsius. 2 mL of a chloroform solution with 1 mg/mL of MEHQ were added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a target compound (1A) was obtained. The yield amount was 8.19 g (20.0 mmol), and the yield was 90.2 k.

Measurement results of $^1$H-NMR ("AVANCE III HD" available from Bruker) being the compound (1A) are shown below.

$^1$H-NMR (500 MHz, DMSO-d6): δ0.94 (6H, s), 1.81 (3H, s), 2.60 (3H, s), 3.30 (2H, s), 3.84 (3H, s), 3.93 (2H, s), 4.53 (2H, s), 5.59 (1H, s), 5.97 (1H, s), 7.10-7.11 (1H, d), 7.67-7.76 (2H, m), 7.74-7.75 (2H, d), 8.00-8.02 (2H, d)

Example 2 (Synthesis of Compound (1B))

(Synthesis of Intermediate Compound (b3))

The intermediate compound (a2) described in Example 1 was used, and thus an intermediate compound (b3) was synthesized. 11.31 g (37.3 mmol) of the intermediate compound (a2), 10.96 g (48.5 mmol) of 4-benzoylphenylboronic acid, and 150 mL of dioxane were measured and put in a 500 milliliter-reactor vessel, and the resultant was stirred to obtain a uniform solution. A dilute solution of 15.42 g (145.4 mmol) of sodium hydrogen carbonate with 75 mL of pure water and 862 mg (0.746 mmol) of a tetrakis(triphenylphosphine)palladium(0) complex were added to the resultant. While water at a temperature of 5 degrees Celsius was caused to flow through a cooling tube, the resultant was stirred at a temperature of 110 degrees Celsius for four hours. After that, the reaction solution was checked with TLC, and disappearance of the intermediate compound (a2) was confirmed. At this point, 100 mL of a 2N ammonium chloride aqueous solution were added to the reaction solution. The resultant was separated into an organic layer and a water layer by a separating funnel, and then the water layer was extracted twice by 35 mL of ethyl acetate. The organic layer and the extracted layer were collectively washed twice with 100 mL of a saturated saline solution, were replaced in a vessel, and anhydrous magnesium sulfate was added.

Solid matters were removed through filtration, and the filtrate was concentrated under a low pressure at a temperature of 50 degrees Celsius. The white-colored solid matters obtained through refining with a silica gel column (a development solvent satisfied n-hexane:ethyl acetate=2:1) were dried under a low pressure at a temperature of 70 degrees Celsius for four hours, and thus an intermediate compound (b3) was obtained. The yield amount was 11.89 g (29.4 mmol), and the yield was 78.8%.

[Formula 14]

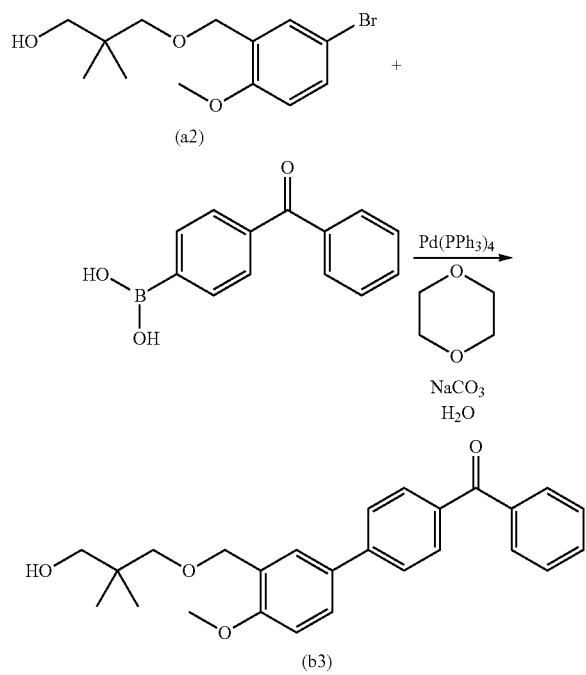

(Synthesis of Target Compound (1B))

11.89 g (29.4 mmol) of the intermediate compound (b3), 7.44 g (73.5 mmol) of triethylamine (Et₃N), 238 mg (1.92 mmol) of 4-methoxyphenol(MEHQ), and 100 mL of tetrahydrofuran (dehydration) were measured and put in a 300 milliliter-reactor vessel. The resultant was stirred to obtain a uniform solution, and was cooled to a temperature of 0 degrees Celsius. 6.15 g (58.8 mmol) of methacryloyl chloride were slowly dropped to the resultant. Stirring was sequentially performed for two hours. After that, the reaction solution was checked with TLC, and substantial disappearance of the intermediate compound (b3) was confirmed. At this point, 100 mL of a 2N sodium hydroxide aqueous solution were added to the reaction solution. The resultant was separated into an organic layer and a water layer by a separating funnel, and then the water layer was extracted twice by 30 mL of ethyl acetate. The organic layer and the extracted layer were collectively washed twice with 100 mL of a saturated saline solution, were replaced in a vessel, and anhydrous magnesium sulfate was added.

Solid matters were removed through filtration, and the filtrate was concentrated under a low pressure at a temperature of 40 degrees Celsius. 2.5 mL of a chloroform solution with 1 mg/mL of MEHQ were added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a target compound (1B) was obtained. The yield amount was 11.65 g (24.7 mmol), and the yield was 83.9%.

[Formula 15]

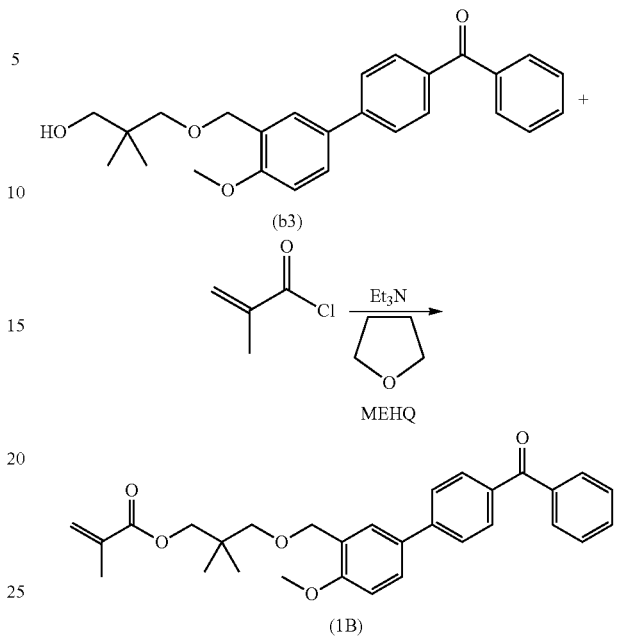

Measurement results of ¹H-NMR ("AVANCE III HD" available from Bruker) being the compound (1B) are shown below.

¹H-NMR (500 MHz, DMSO-d6): δ0.94 (6H, s), 1.81 (3H, s), 3.30 (2H, s), 3.84 (3H, s), 3.94 (2H, s), 4.54 (2H, s), 5.59 (1H, s), 5.96 (1H, s), 7.11-7.12 (1H, d), 7.56-7.82 (11H, m)

Example 3 (Synthesis of Compound (1C))

(Synthesis of Intermediate Compound (c2))

The intermediate compound (a1) described in Example 1 was used, and thus an intermediate compound (c2) was synthesized. 1.30 g (32.6 mmol) of sodium hydride (NaH; concentration of 60%) and 75 mL of tetrahydrofuran (dehydration) were measured and put in a 300 milliliter-reactor vessel, and the resultant was cooled to a temperature of 0 degree Celsius. A dilute solution of 6.79 g (65.2 mmol) of 1,5-pentanediol with 15 mL of tetrahydrofuran was slowly dropped to the resultant. After stirring at a room temperature for an hour, a dilute solution of 6.08 g (21.7 mmol) of the intermediate compound (a1) with 10 mL of tetrahydrofuran was added rapidly. After stirring at a temperature of 60 degrees Celsius for five hours, the reaction solution was checked with TLC, and disappearance of the intermediate compound (a1) was confirmed. At this point, 100 mL of 2N hydrochloric acid were added to the reaction solution. The resultant was separated into an organic layer and a water layer by a separating funnel, and then the water layer was extracted twice by 25 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 50 degrees Celsius. The slightly yellow-colored liquid obtained through refining with a silica gel column (a development solvent satisfied n-hexane:ethyl acetate=1:1) was dried under a low pressure at a temperature of 70 degrees Celsius for four hours, and thus an intermediate compound (c2) was obtained. The yield amount was 4.14 g (13.7 mmol), and the yield was 62.9%.

[Formula 16]

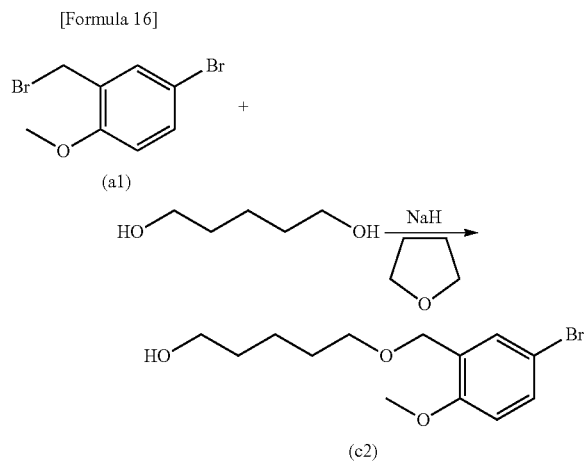

(Synthesis of Intermediate Compound (c3))

4.14 g (13.7 mmol) of the intermediate compound (c2), 4.01 g (17.8 mmol) 4-benzoylphenylboronic acid, and 50 mL of dioxane were measured and put in a 300 milliliter-reactor vessel, and the resultant was stirred to obtain a uniform solution. A dilute solution of 5.64 g (53.2 mmol) of sodium hydrogen carbonate with 25 mL of pure water and 316 mg (0.273 mmol) of a tetrakis(triphenylphosphine) palladium(0) complex were added to the resultant. While water at a temperature of 5 degrees Celsius was caused to flow through a cooling tube, the resultant was stirred at a temperature of 110 degrees Celsius for four hours. After that, the reaction solution was checked with TLC, and disappearance of the intermediate compound (c2) was confirmed. At this point, 30 mL of a 2N ammonium chloride aqueous solution were added to the reaction solution. The resultant was separated into an organic layer and a water layer by a separating funnel, and then the water layer was extracted twice by 15 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 50 degrees Celsius. The light yellow-colored liquid obtained through refining with a silica gel column (a development solvent satisfied n-hexane:ethyl acetate=1:1) was dried under a low pressure at a temperature of 70 degrees Celsius for four hours, and thus an intermediate compound (c3) was obtained. The yield amount was 3.73 g (9.22 mmol), and the yield was 67.5 k.

[Formula 17]

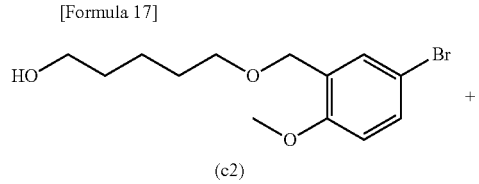

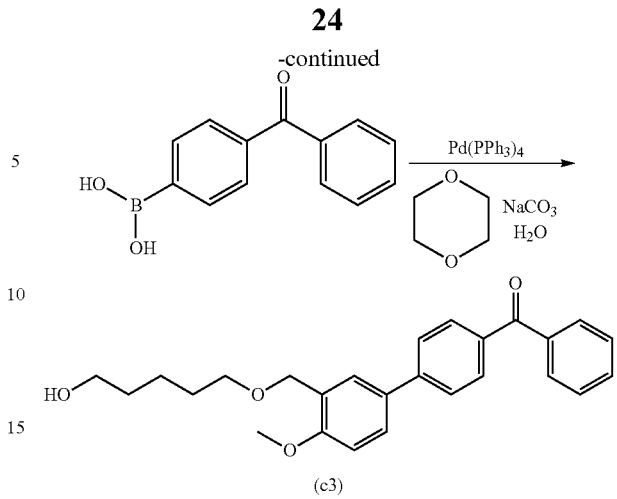

(Synthesis of Target Compound (1C))

3.73 g (9.22 mmol) of the intermediate compound (c3), 2.33 g (23.1 mmol) of triethylamine (Et₃N), 74.6 mg (0.601 mmol) of 4-methoxyphenol (MEHQ), and 30 mL of tetrahydrofuran (dehydration) were measured and put in a 100 milliliter-reactor vessel. The resultant was stirred to obtain a uniform solution, and was cooled to a temperature of 0 degrees Celsius. 1.93 g (18.4 mmol) of methacryloyl chloride were slowly dropped to the resultant. Stirring was sequentially performed for two hours. After that, the reaction solution was checked with TLC, and the intermediate compound (c3) disappeared. At this point, 30 mL of a 2N sodium hydroxide aqueous solution were added to the reaction solution. The resultant was separated into an organic layer and a water layer by a separating funnel, and then the water layer was extracted twice by 10 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 40 degrees Celsius. 1 mL of a chloroform solution with 1 mg/mL of MEHQ was added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a target compound (1C) was obtained. The yield amount was 3.71 g (7.85 mmol), and the yield was 85.1%.

[Formula 18]

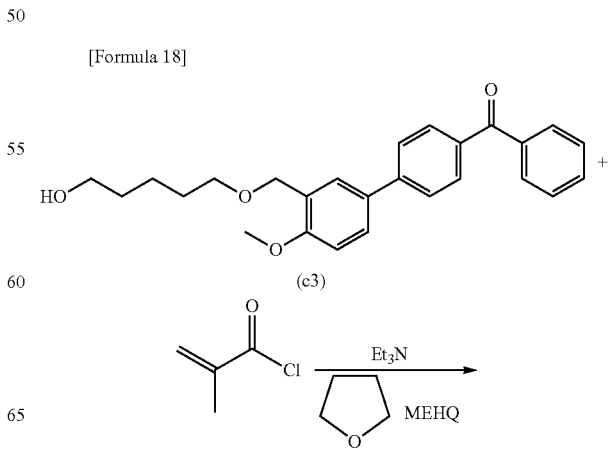

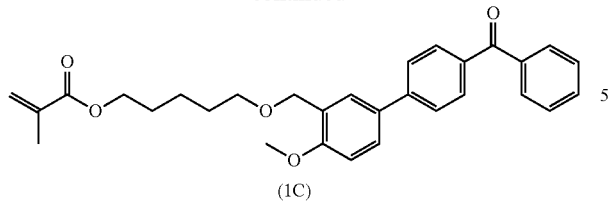

(1C)

Measurement results of ¹H-NMR ("AVANCE III HD" available from Bruker) being the compound (1C) are shown below.

¹H-NMR (500 MHz, DMSO-d6): δ1.39-1.45 (2H, m), 1.56-1.67 (4H, m), 1.83 (3H, s), 3.50-3.52 (2H, t), 3.85 (3H, s), 4.07-4.10 (2H, t), 4.52 (2H, s), 5.60 (1H, s), 5.98 (1H, s), 7.12-7.14 (1H, d), 7.57-7.83 (11H, m)

Example 4 (Synthesis of Compound (1D))

(Synthesis of Intermediate Compound (d2))

The intermediate compound (a1) described in Example 1 was used, and thus an intermediate compound (d2) was synthesized. 1.30 g (32.6 mmol) of sodium hydride (NaH; concentration of 60%) and 75 mL of tetrahydrofuran (dehydration) were measured and put in a 300 milliliter-reactor vessel, and the resultant was cooled to a temperature of 0 degree Celsius. A dilute solution of 6.91 g (65.2 mmol) of diethyleneglycol with 15 mL of tetrahydrofuran was slowly dropped to the resultant. After stirring at a room temperature for an hour, a dilute solution of 6.08 g (21.7 mmol) of the intermediate compound (a1) with 10 mL of tetrahydrofuran was added rapidly. The resultant was stirred at a temperature of 60 degrees Celsius for three hours. After that, the reaction solution was checked with TLC, and disappearance of the intermediate compound (a1) was confirmed. At this point, 100 mL of 2N hydrochloric acid were added to the reaction solution. The resultant was separated into an organic layer and a water layer by a separating funnel, and then the water layer was extracted twice by 25 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 50 degrees Celsius. The slightly yellow-colored liquid obtained through refining with a silica gel column (a development solvent satisfied n-hexane:ethyl acetate=1:4) was dried under a low pressure at a temperature of 70 degrees Celsius for four hours, and thus an intermediate compound (d2) was obtained. The yield amount was 4.14 g (13.6 mmol), and the yield was 62.5%.

[Formula 19]

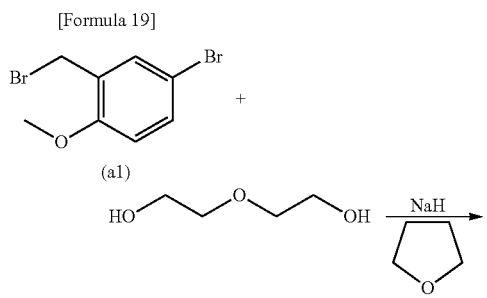

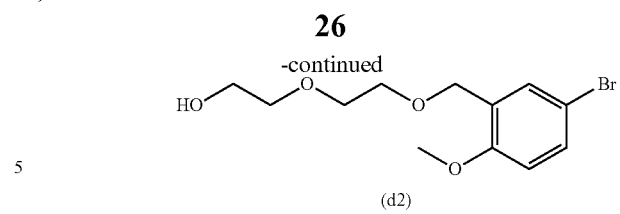

(d2)

(Synthesis of Intermediate Compound (d3))

4.14 g (13.6 mmol) of the intermediate compound (c2), 3.99 g (17.6 mmol) of 4-benzoylphenylboronic acid, and 50 mL of dioxane were measured and put in a 300 milliliter-reactor vessel, and the resultant was stirred to obtain a uniform solution. A dilute solution of 5.61 g (52.9 mmol) of sodium hydrogen carbonate with 25 mL of pure water and 314 mg (0.271 mmol) of a tetrakis(triphenylphosphine) palladium(0) complex were added to the resultant. While water at a temperature of 5 degrees Celsius was caused to flow through a cooling tube, the resultant was stirred at a temperature of 110 degrees Celsius for four hours. After that, the reaction solution was checked with TLC, and disappearance of the intermediate compound (d2) was confirmed. At this point, 30 mL of a 2N ammonium chloride aqueous solution were added to the reaction solution. The resultant was separated into an organic layer and a water layer by a separating funnel, and then the water layer was extracted twice by 15 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 50 degrees Celsius. The light yellow-colored liquid obtained through refining with a silica gel column (a development solvent satisfied n-hexane:ethyl acetate=1:4) was dried under a low pressure at a temperature of 70 degrees Celsius for four hours, and thus an intermediate compound (d3) was obtained. The yield amount was 3.87 g (9.52 mmol), and the yield was 70.2%.

[Formula 20]

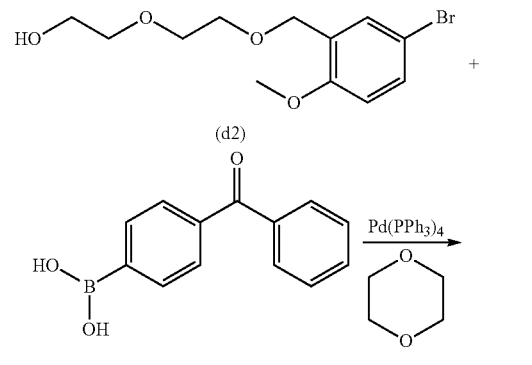

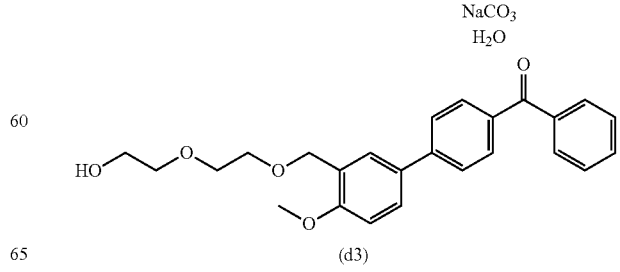

(d3)

(Synthesis of Target Compound (1D))

3.87 g (9.52 mmol) of the intermediate compound (d3), 2.41 g (23.8 mmol) of triethylamine (Et₃N), 77.4 mg (0.623 mmol) of 4-methoxyphenol (MEHQ), and 30 mL of tetrahydrofuran (dehydration) were measured and put in a 100 milliliter-reactor vessel. The resultant was stirred to obtain a uniform solution, and was cooled to a temperature of 0 degrees Celsius. 1.99 g (19.0 mmol) of methacryloyl chloride were slowly dropped to the resultant. Stirring was sequentially performed for two hours. After that, the reaction solution was checked with TLC, and disappearance of the intermediate compound (d3) was confirmed. At this point, 30 mL of a 2N sodium hydroxide aqueous solution were added to the reaction solution. The resultant was separated into an organic layer and a water layer by a separating funnel, and then the water layer was extracted twice by 10 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 40 degrees Celsius. 1 mL of a chloroform solution with 1 mg/mL of MEHQ was added to the slightly yellow-colored liquid obtained through refining with a silica gel column (a development solvent satisfied n-hexane:ethyl acetate=2:1), and the resultant was dried under a low pressure at a temperature of 40 degrees Celsius for three hours. Thus, a target compound (1D) was obtained. The yield amount was 4.02 g (8.47 mmol), and the yield was 88.9%.

[Formula 21]

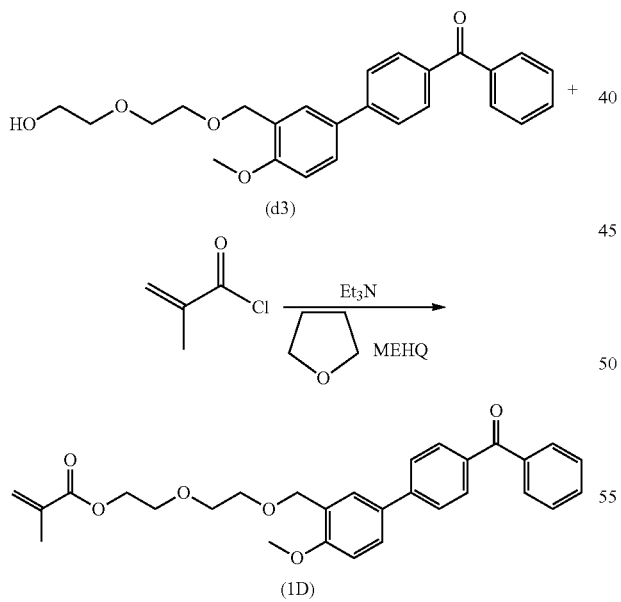

(d3)

(1D)

Measurement results of $^1$H-NMR ("AVANCE III HD" available from Bruker) being the compound (1D) are shown below.

$^1$H-NMR (500 MHz, DMSO-d6): δ1.82 (3H, s), 3.65-3.70 (6H, m), 3.85 (3H, s), 4.21-4.23 (2H, t), 4.57 (2H, s), 5.60 (1H, s), 5.98 (1H, s), 7.12-7.13 (1H, d), 7.57-7.81 (11H, m)

Example 5 (Synthesis of Compound (1E))

(Synthesis of Intermediate Compound (e2))

The intermediate compound (a1) described in Example 1 was used, and thus an intermediate compound (e2) was synthesized. 1.30 g (32.6 mmol) of sodium hydride (NaH; concentration of 60%) and 75 mL of tetrahydrofuran (dehydration) were measured and put in a 300 milliliter-reactor vessel, and the resultant was cooled to a temperature of 0 degree Celsius. A dilute solution of 13.82 g (65.2 mmol) of 2,2,3,3,4,4-hexafluoro-1,5-pentanediol with 15 mL of tetrahydrofuran was slowly dropped to the resultant. After stirring at a room temperature for an hour, a dilute solution of 6.08 g (21.7 mmol) of the intermediate compound (a1) with 10 mL of tetrahydrofuran was added rapidly. The resultant was stirred at a temperature of 60 degrees Celsius for three hours. After that, the reaction solution was checked with TLC, and disappearance of the intermediate compound (a1) was confirmed. At this point, 100 mL of 2N hydrochloric acid were added to the reaction solution. The resultant was separated into an organic layer and a water layer by a separating funnel, and then the water layer was extracted twice by 25 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 50 degrees Celsius. The slightly yellow-colored liquid obtained through refining with a silica gel column (a development solvent satisfied n-hexane:ethyl acetate=3:1) was dried under a low pressure at a temperature of 70 degrees Celsius for four hours, and thus an intermediate compound (e2) was obtained. The yield amount was 7.62 g (15.6 mmol), and the yield was 72.0%.

[Formula 22]

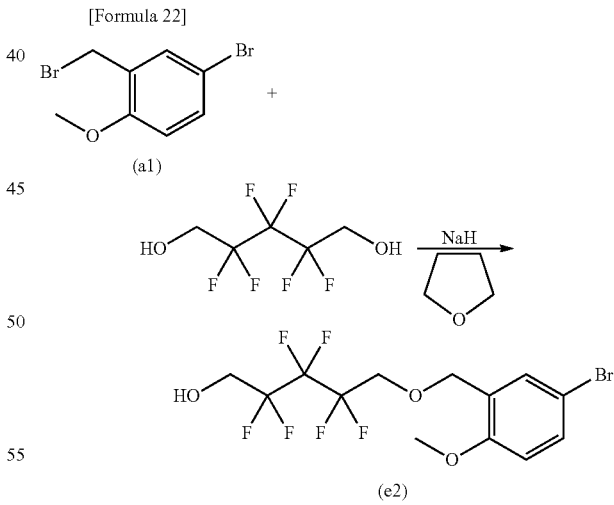

(a1)

(e2)

(Synthesis of Intermediate Compound (e3))

7.62 g (15.6 mmol) of the intermediate compound (e2), 34.60 g (20.3 mmol) of 4-benzoylphenylboronic acid, and 60 mL of dioxane were measured and put in a 300 milliliter-reactor vessel, and the resultant was stirred to obtain a uniform solution. A dilute solution of 6.46 g (61.0 mmol) of sodium hydrogen carbonate with 30 mL of pure water and 361 mg (0.313 mmol) of a tetrakis(triphenylphosphine) palladium(0) complex were added to the resultant. While water at a temperature of 5 degrees Celsius was caused to flow through a cooling tube, the resultant was stirred at a temperature of 110 degrees Celsius for four hours. After that, the reaction solution was checked with TLC, and disappearance of the intermediate compound (e2) was confirmed. At this point, 40 mL of a 2N ammonium chloride aqueous solution were added to the reaction solution. The resultant was separated into an organic layer and a water layer by a separating funnel, and then the water layer was extracted twice by 20 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 50 degrees Celsius. The light yellow-colored liquid obtained through refining with a silica gel column (a development solvent satisfied n-hexane:ethyl acetate=2:1) was dried under a low pressure at a temperature of 70 degrees Celsius for four hours, and thus an intermediate compound (e3) was obtained. The yield amount was 7.11 g (13.9 mmol), and the yield was 88.7%.

[Formula 23]

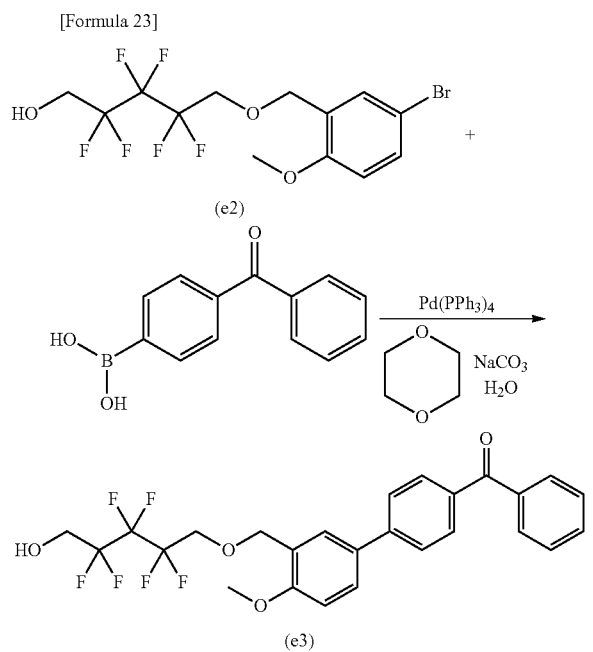

(Synthesis of Target Compound (1E))

7.11 g (13.9 mmol) of the intermediate compound (e3), 3.51 g (34.7 mmol) of triethylamine (Et₃N), 142 mg (1.14 mmol) of 4-methoxyphenol (MEHQ), and 40 mL of tetrahydrofuran (dehydration) were measured and put in a 100 milliliter-reactor vessel. The resultant was stirred to obtain a uniform solution, and was cooled to a temperature of 0 degrees Celsius. 2.90 g (27.7 mmol) of methacryloyl chloride were slowly dropped to the resultant. Stirring was sequentially performed for two hours. After that, the reaction solution was checked with TLC, and complete disappearance of the intermediate compound (e3) was confirmed. At this point, 40 mL of a 2N sodium hydroxide aqueous solution were added to the reaction solution. The resultant was separated into an organic layer and a water layer by a separating funnel, and then the water layer was extracted twice by 15 mL of ethyl acetate. The organic layer and the extracted layer were collectively washed twice with 50 mL of a saturated saline solution, were replaced in a vessel, and anhydrous magnesium sulfate was added.

Solid matters were removed through filtration, and the filtrate was concentrated under a low pressure at a temperature of 40 degrees Celsius. 1.5 mL of a chloroform solution with 1 mg/mL of MEHQ was added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a target compound (1E) was obtained. The yield amount was 6.63 g (11.4 mmol), and the yield was 82.3%. Note that, when being left at a room temperature, the target compound (1E) was slowly crystallized. The melting point was at a temperature of 44 degrees Celsius.

[Formula 24]

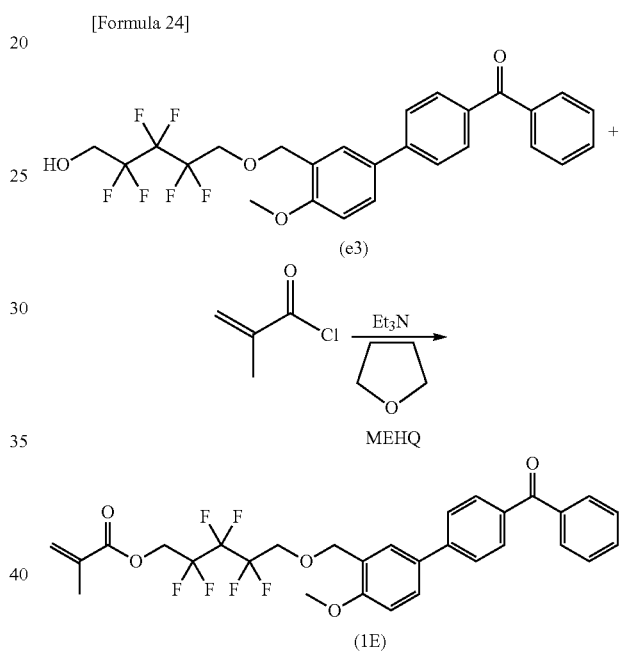

Measurement results of ¹H-NMR ("AVANCE III HD" available from Bruker) being the compound (1E) are shown below.

¹H-NMR (500 MHz, DMSO-d6): δ1.89 (3H, s), 3.87 (3H, s), 4.19-4.25 (2H, t), 4.74 (2H, s), 4.80-4.86 (2H, t), 5.79 (1H, s), 6.10 (1H, s), 7.16-7.18 (1H, d), 7.57-7.84 (11H, m)

Example 6 (Synthesis of Compound (1F))

(Synthesis of Intermediate Compound (f3))

The intermediate compound (a2) described in Example 1 was used, and thus an intermediate compound (f3) was synthesized. 10.07 g (33.2 mmol) of the intermediate compound (a2), 6.47 g (43.2 mmol) of 4-formylphenylboronic acid, and 150 mL of dioxane were measured and put in a 500 milliliter-reactor vessel, and the resultant was stirred to obtain a uniform solution. A dilute solution of 13.73 g (129.5 mmol) of sodium hydrogen carbonate with 75 mL of pure water and 768 mg (0.664 mmol) of a tetrakis(triphenylphosphine)palladium(0) complex were added to the resultant. While water at a temperature of 5 degrees Celsius was caused to flow through a cooling tube, the resultant was stirred at a temperature of 110 degrees Celsius for four hours. After that, the reaction solution was checked with TLC, and complete disappearance of the intermediate compound (a2) was confirmed. At this point, 100 mL of a 2N ammonium chloride aqueous solution were added to the reaction solution. The resultant was separated into an organic layer and a water layer by a separating funnel, and then the water layer was extracted twice by 30 mL of ethyl acetate. The organic layer and the extracted layer were collectively washed twice with 100 mL of a saturated saline solution. The resultant was replaced in a vessel, and anhydrous magnesium sulfate was added.

Solid matters were removed through filtration, and the filtrate was concentrated under a low pressure at a temperature of 50 degrees Celsius. The white-colored solid matters obtained through refining with a silica gel column (a development solvent satisfied n-hexane:ethyl acetate=2:1) were dried under a low pressure at a temperature of 70 degrees Celsius for four hours, and thus an intermediate compound (f3) was obtained. The yield amount was 7.68 g (23.4 mmol), and the yield was 70.4%.

[Formula 25]

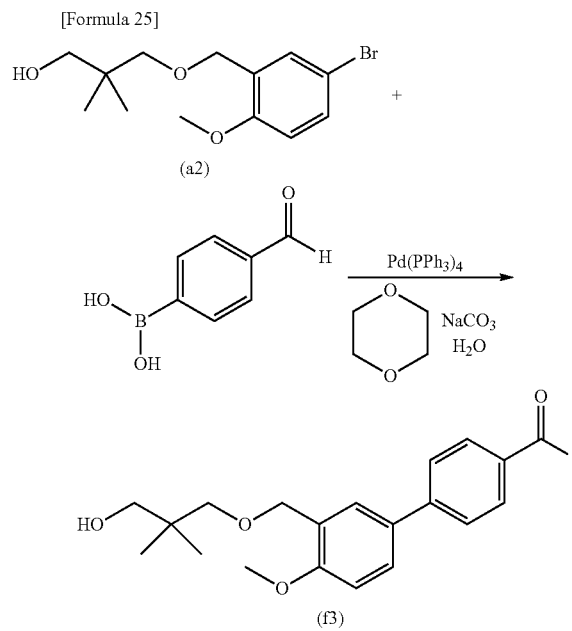

(Synthesis of Target Compound (1F))

3.77 g (11.5 mmol) of the intermediate compound (f3), 2.90 g (28.7 mmol) of triethylamine (Et₃N), 75.4 mg (0.607 mmol) of 4-methoxyphenol (MEHQ), and 40 mL of tetrahydrofuran (dehydration) were measured and put in a 100 milliliter-reactor vessel. The resultant was stirred to obtain a uniform solution, and was cooled to a temperature of 0 degrees Celsius. 2.40 g (23.0 mmol) of methacryloyl chloride were slowly dropped to the resultant. Stirring was sequentially performed for two hours. After that, the reaction solution was checked with TLC, and substantial disappearance of the intermediate compound (f3) was confirmed. At this point, 40 mL of a 2N sodium hydroxide aqueous solution were added to the reaction solution. The resultant was separated into an organic layer and a water layer by a separating funnel, and then the water layer was extracted twice by 20 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees Celsius. 1 mL of a chloroform solution with 1 mg/mL of MEHQ was added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a target compound (1F) was obtained. The yield amount was 3.77 g (9.51 mmol), and the yield was 82.8%.

[Formula 26]

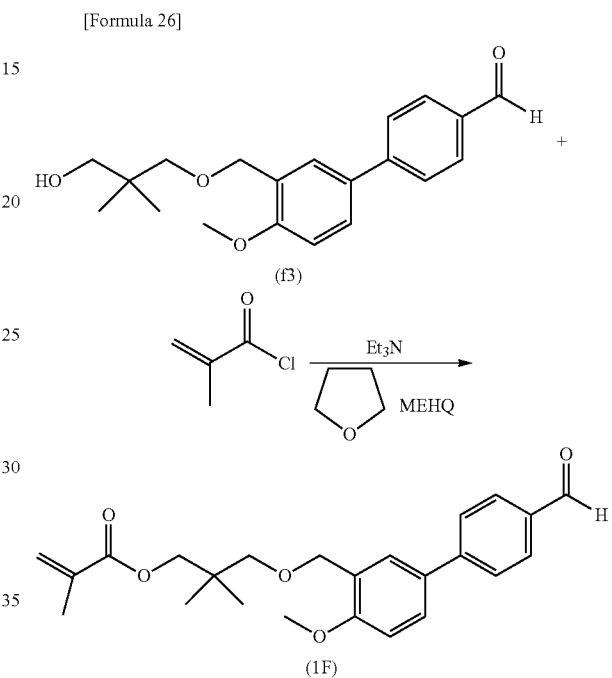

Measurement results of ¹H-NMR ("AVANCE III HD" available from Bruker) being the compound (1F) are shown below.

¹H-NMR (500 MHz, DMSO-d6): δ0.93 (6H, s), 1.80 (3H, s), 3.29 (2H, s), 3.83 (3H, s), 3.92 (2H, s), 4.52 (2H, s), 5.57 (1H, s), 5.95 (1H, s), 7.09-7.11 (1H, d), 7.67-7.69 (2H, m), 7.81-7.82 (2H, d), 7.94-7.96 (2H, d), 10.02 (1H, s)

Example 7 (Synthesis of Compound (1G))

(Synthesis of Intermediate Compound (g2))

The intermediate compound (a1) described in Example 1 was used, and thus an intermediate compound (g2) was synthesized. 1.27 g (31.8 mmol) of sodium hydride (NaH; concentration of 60%) and 75 mL of tetrahydrofuran (dehydration) were measured and put in a 300 milliliter-reactor vessel, and the resultant was cooled to a temperature of 0 degree Celsius. A dilute solution of 3.95 g (63.7 mmol) of ethyleneglycol with 15 mL of tetrahydrofuran was slowly dropped to the resultant. After stirring at a room temperature for an hour, a dilute solution of 5.94 g (21.2 mmol) of the intermediate compound (a1) with 10 mL of tetrahydrofuran was added rapidly. The resultant was stirred at a temperature of 60 degrees Celsius for 22 hours. After that, the reaction solution was checked with TLC, and the intermediate compound (a1) disappeared. At this point, 100 mL of 2N hydrochloric acid were added to the reaction solution. The resultant was separated into an organic layer and a water layer by a separating funnel, and then the water layer was extracted twice by 15 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 50 degrees Celsius. The yellow-colored liquid obtained through refining with a silica gel column (a development solvent satisfied n-hexane:ethyl acetate=1:1) was dried under a low pressure at a temperature of 70 degrees Celsius for four hours, and thus an intermediate compound (g2) was obtained. The yield amount was 3.52 g (13.4 mmol), and the yield was 63.5%.

[Formula 27]

(Synthesis of Intermediate Compound (g3))

3.52 g (13.4 mmol) of the intermediate compound (g2), 2.20 g (13.4 mmol) of 4-acetylphenylboronic acid, and 40 mL of dioxane were measured and put in a 300 milliliter-reactor vessel, and the resultant was stirred to obtain a uniform solution. A dilute solution of 4.19 g (40.5 mmol) of sodium hydrogen carbonate with 20 mL of pure water and 239 mg (0.206 mmol) of a tetrakis(triphenylphosphine)palladium(0) complex were added to the resultant. While water at a temperature of 5 degrees Celsius was caused to flow through a cooling tube, the resultant was stirred at a temperature of 110 degrees Celsius for four hours. After that, the reaction solution was checked with TLC, and the intermediate compound (g2) completely disappeared. At this point, 30 mL of a 2N ammonium chloride aqueous solution were added to the reaction solution. The resultant was separated into an organic layer and a water layer by a separating funnel, and then the water layer was extracted twice by 15 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 50 degrees Celsius. The yellow-colored liquid obtained through refining with a silica gel column (a development solvent satisfied n-hexane:ethyl acetate=1:2) was dried under a low pressure at a temperature of 70 degrees Celsius for four hours, and thus an intermediate compound (g3) was obtained. The yield amount was 2.83 g (9.42 mmol), and the yield was 69.9%.

[Formula 28]

(Synthesis of Target Compound (1G))

2.83 g (9.42 mmol) of the intermediate compound (g3), 2.38 g (23.6 mmol) of triethylamine (Et₃N), 56.6 mg (0.456 mmol) of 4-methoxyphenol (MEHQ), and 30 mL of tetrahydrofuran (dehydration) were measured and put in a 100 milliliter-reactor vessel. The resultant was stirred to obtain a uniform solution, and was cooled to a temperature of 0 degrees Celsius. 1.97 g (18.8 mmol) of methacryloyl chloride were slowly dropped to the resultant. Stirring was sequentially performed for an hour. After that, the reaction solution was checked with TLC, and the intermediate compound (g3) completely disappeared. At this point, 30 mL of a 2N sodium hydroxide aqueous solution were added to the reaction solution. The resultant was separated into an organic layer and a water layer by a separating funnel, and then the water layer was extracted twice by 10 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees Celsius. 1 mL of a chloroform solution with 1 mg/mL of MEHQ was added to the slightly yellow-colored liquid obtained through refining with a silica gel column (a development solvent satisfied n-hexane:ethyl acetate=2:1), and the resultant was dried under a low pressure at a temperature of 40 degrees Celsius for three hours. Thus, a target compound (1G) was obtained. The yield amount was 3.14 g (8.52 mmol), and the yield was 90.5%.

[Formula 29]

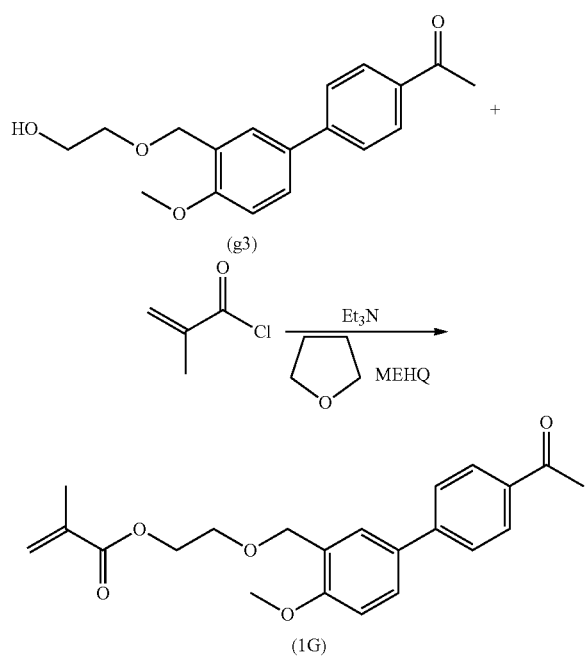

Measurement results of $^1$H-NMR ("AVANCE III HD" available from Bruker) being the compound (1G) are shown below.

$^1$H-NMR (500 MHz, DMSO-d6): δ1.85 (3H, s), 2.60 (3H, s), 3.74-3.76 (2H, t), 3.84 (3H, s), 4.29-4.31 (2H, t), 4.59 (2H, s), 5.64 (1H, s), 6.02 (1H, s), 7.10-7.12 (1H, d), 7.66-7.69 (2H, m), 7.74-7.76 (2H, d), 7.99-8.01 (2H, d)

<Physical Property Evaluation of Compound>
(Production of Sample for Refractive Index Measurement)

The obtained compound was heated and melted to be in a liquid state, and then was cooled and solidified. Thus, a sample for refractive index measurement was obtained.

(Measurement and Evaluation)

A refractive index was measured by using a multi-wavelength refractometer (manufactured by Anton Paar Japan). Refractive indexes $n_C$, $n_d$, $n_F$, and $n_g$ were measured respectively for a C-line (having a wavelength of 656.3 nm), a d-line (having a wavelength of 587.6 nm), an F-line (having a wavelength of 486.1 nm), and a g-line (having a wavelength of 435.8 nm). Further, a $θ_{g,F}$ value and a $v_d$ value were calculated from the expressions given below.

$$θ_{g,F}=(n_g-n_F)/(n_F-n_C)$$

$$v_d=(n_d-1)/(n_F-n_C)$$

II. Production of Resin Precursor and Physical Property Evaluation
(Production of Main Agent 3)

First, a main agent 3 (a compound represented by Formula (iii)) described later was produced in accordance with the following method.

First, in an argon gas flow, 10.00 g(55.6 mmol) of 3-formyl-4-methoxyphenylboronic acid, 50 mL of tetrahydrofuran (THF, dehydration), and 50 mL of ethanol(dehydration) were measured and put in a 300 milliliter-reactor vessel, and the resultant was stirred at a temperature of 0 degree Celsius. 1.36 g (36.0 mmol) of sodium borohydride (NaBH$_4$) were added to the resultant by a small amount each. After stirring at a degree of 0 degrees Celsius for two hours, the reaction check was performed with TLC, and disappearance of the raw materials was confirmed. Immediately after 50 mL of city water was added to the resultant to stop the reaction, white precipitate was generated promptly.

Subsequently, the suspension was subjected to filtration under a low pressure, and an organic solvent was removed. Hydrochloric acid having a concentration of 2 mol/L was added until the suspension became neutral. After that, the precipitate was recovered through filtration. The recovered matters through filtration were washed with 50 mL of ethyl acetate, and were dried under a low pressure at a temperature of 40 degrees Celsius. Thus, as the recovered matters, an intermediate compound (iii-1) ((3-hydroxymethyl)-4-methoxy-phenyl)boronic acid) was obtained. The yield amount was 9.27 g (50.9 mmol), and the yield was 91.5%.

[Formula 30]

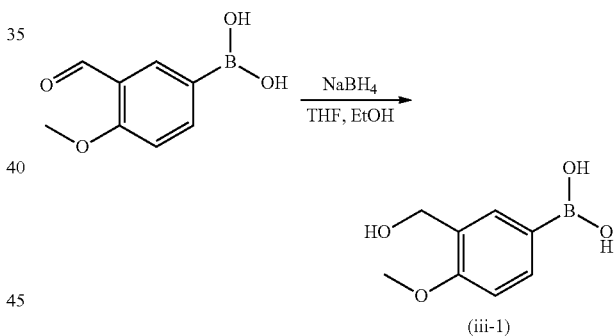

Subsequently, 3.30 g (12.5 mmol) of 4,4'-dichlorobenzophenone, 5.00 g (27.5 mmol) of the intermediate compound (a1), 3.57 g (42.5 mmol) of sodium hydrogen carbonate, 150 mL of 1,4-dioxane, and 75 mL of distilled water were measured and put in a 500 milliliter-reactor vessel, and the

TABLE 1

| | Example 1 | Example 2 | Example 3 | Example 4 | Example 5 | Example 6 | Example 7 |
|---|---|---|---|---|---|---|---|
| | | | | Name of compound | | | |
| | 1A | 1B | 1C | 1D | 1E | 1F | 1G |
| $n_C$ | 1.5639 | 1.5903 | 1.5937 | 1.5957 | 1.5497 | 1.5712 | 1.5840 |
| $n_d$ | 1.5716 | 1.5992 | 1.6026 | 1.6046 | 1.5575 | 1.5796 | 1.5930 |
| $n_F$ | 1.5920 | 1.6230 | 1.6269 | 1.6289 | 1.5789 | 1.6040 | 1.6156 |
| $n_g$ | 1.6123 | 1.6474 | 1.6507 | 1.6536 | 1.6002 | 1.6288 | 1.6385 |
| $θ_{g,F}$ | 0.722 | 0.746 | 0.717 | 0.744 | 0.729 | 0.756 | 0.725 |
| $v_d$ | 20.3 | 18.3 | 18.2 | 18.2 | 19.1 | 17.7 | 18.8 | resultant was subjected to argon bubbling while being stirred at a room temperature. After stirred for 30 minutes, 0.29 g (0.25 mmol) of tetrakis(triphenylphosphine)palladium(Pd (Ph$_3$)$_4$) were added to the reaction system. Further, argon bubbling was switched to an argon gas flow, and stirring was performed at a temperature of 90 degrees Celsius over one night. After that, the reaction check was performed with TLC, disappearance of the raw materials was confirmed, and then heating was stopped. After the reaction solution was left and cooled to a room temperature, 25 mL of a saturated ammonium chloride aqueous solution and 150 mL of city water were added, and the resultant was stirred for 30 minutes. The deposited precipitate was recovered through filtration, was washed with 300 mL of water, and thus yellowish-white powder was obtained.

The obtained yellowish-white powder was dried under a low pressure at a temperature of 70 degrees Celsius over one night. 900 mL of a mixed solution in which tetrahydrofuran:chloroform=1:9 was satisfied were added to the powder, and the resultant was heated at a temperature of 60 degrees Celsius. The solution was refined with a silica gel column (a development solvent satisfied tetrahydrofuran:chloroform=1:9), and thus an intermediate compound (iii-2) was obtained. The yield amount was 4.86 g (10.7 mmol), and the yield was 85.6%.

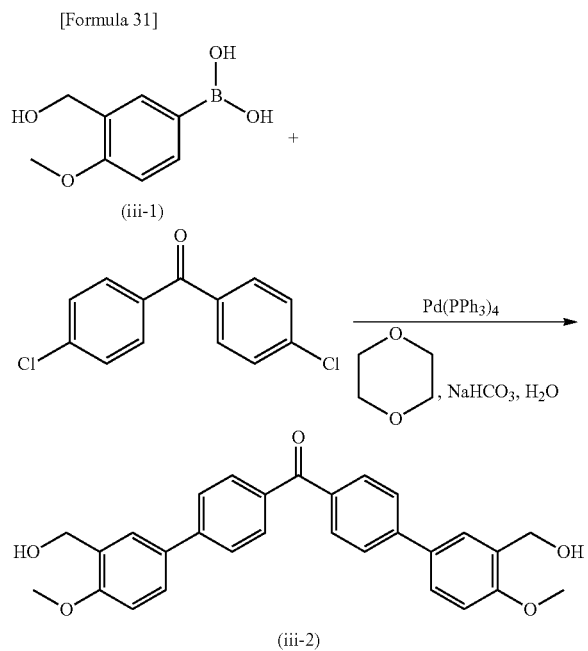

[Formula 31]

(iii-1)

(iii-2)

Further, in an argon gas flow, 2 g (4.40 mmol) of the intermediate compound (a2) and 80 mL of dichloromethane (dehydration) were measured and put in a 200 milliliter-reactor vessel, and the resultant was cooled to a temperature of 0 degree Celsius. 1.01 g (3.74 mmol) of phosphorus tribromide (PBr$_3$) were dropped to the resultant for five minutes, and a temperature thereof was increased to a room temperature. After stirring for three hours, the reaction check was performed with TLC and the HPLC analysis, disappearance of the raw materials was confirmed, and then stirring was stopped. 80 mL of city water at a temperature of 10 degrees Celsius or below were added to the resultant, and stirring was performed again for 30 minutes. Further, after the deposited precipitate was recovered through filtration, the filtrate was separated into an organic layer and a water layer. The water layer was washed twice with 50 mL of dichloromethane, and thus an organic component dissolved in the water layer was recovered. Subsequently, the organic layer and the organic components recovered from the water layer were mixed to be a mixed solution. The mixed solution was subjected to sucking filtration. Note that, at the time of sucking filtration, the water was frozen, which stopped filtration, and hence an operation was carried out while warming the water from above the funnel.

After the obtained filtrate was concentrated under a low pressure, the recovered matters through filtration were added again, and 50 mL of tetrahydrofuran were added to the resultant for suspension. With this, the suspension was obtained. 200 mL of city water was added to the obtained suspension, and the deposited precipitate was recovered through filtration. Regarding the filtrate, after washing with city water until the filtrate became neutral, washing with 20 mL of methanol was further performed. The obtained white powder was dried under a low pressure at a temperature of 70 degrees Celsius over one night. Thus, an intermediate compound (iii-3) was obtained. The yield amount was 2.36 g (4.07 mmol), and the yield was 92.5%.

[Formula 32]

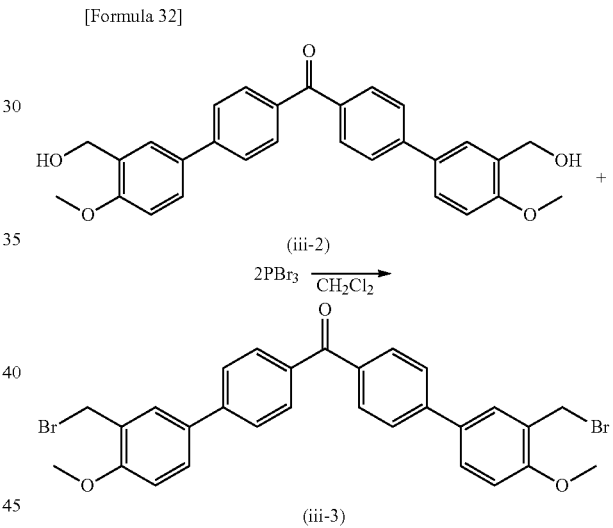

(iii-2)

(iii-3)

The intermediate compound (iii-3) was used, and thus an intermediate compound (iii-4) was synthesized. In an argon gas flow, 300 mL of tetrahydrofuran (dehydration) and 2.33 g (58.5 mmol) sodium hydride (concentration of 60%) were measured and put in a 1000 milliliter-reactor vessel, and the resultant was cooled with ice. A dilute solution of 12.8 g (206 mmol) of ethyleneglycol with 100 mL of tetrahydrofuran was dropped to the resultant, and a temperature thereof was increased to a room temperature. After stirring for an hour, 10 g (17.2 mmol) of the intermediate compound (iii-3) were added at once, and the resultant was heated to a temperature of 60 degrees Celsius. After heating and stirring over one night, the reaction check was performed with TLC, and disappearance of the raw materials was confirmed. 400 mL of city water was added to the resultant, and the reaction was stopped. Separation into an organic layer and a water layer was performed by adding 400 mL of ethyl acetate to the reaction solution. The water layer was washed twice with 200 mL of ethyl acetate, and thus an organic component was recovered from the water layer. Further, the organic layer and the organic components recovered from the water layer were mixed to be a mixed solution. The obtained mixed solution was washed subsequently with water and a saturated saline solution, and then was dried with magnesium sulfate.

Subsequently, the dried mixed solution was concentrated under a low pressure, and the solvent was distillated. With this, 11.3 g of pale yellow-colored solid matters were obtained. The resultant was refined with an NH gel column (a development: chloroform), and the intermediate compound (iii-3) being white solid matters was obtained. The obtained intermediate compound (iii-3) was dried under a low pressure at a temperature of 80 degrees Celsius over one night. The yield amount was 5.01 g (9.23 mmol), and the yield was 53.7%.

[Formula 33]

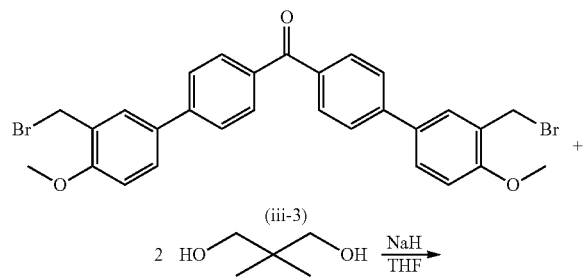

(iii-3)

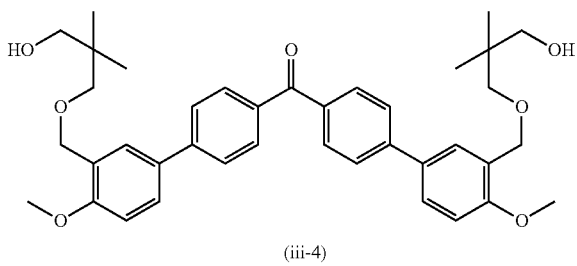

(iii-4)

The steps described above were repeated until the intermediate compound (iii-3) was obtained by 10.7 g in total. Then, in an argon gas flow, 10.7 g of the intermediate compound (iii-3), 90 mL of chloroform(dehydration), 18.9 g (187 mmol) of triethylamine, and 49.0 mg (395 μmol) of p-methoxyphenol addition were measured and put in a 200 milliliter-reactor vessel, and the resultant was cooled at a temperature of 0 degree Celsius. When 7.00 g (67.0 mmol) of methacryloylchloride were dropped to the resultant for five minutes, the solution color was changed to pink, and triethylamine hydrochloride was disposed. Subsequently, a temperature was increased from 0 degree Celsius to a room temperature, and stirring was performed for an hour. After that, the reaction check was performed with TLC and the HPLC analysis, and disappearance of the raw materials was confirmed. 200 mL of city water was added to the resultant, and the reaction was stopped. Subsequently, the reaction solution was separated into an organic layer and a water layer. The water layer was washed twice with 60 mL of chloroform, and thus an organic component dissolved in the water layer was recovered. The obtained organic layer and the organic components recovered from the water layer were mixed to be a mixed solution. The mixed solution was washed subsequently with water and a saturated saline solution, and then was dried with sodium sulfate.

Subsequently, 49.0 mg (395 mmol) of p-methoxyphenol and 20 mL of toluene were added in a dried mixing vessel. Further, the mixed solution was concentrated under a low pressure, and triethylamine and the solvent were distillated. With this, 17.0 g of a crude matter were obtained. The obtained crude matter was refined with a silica gel column (a development solvent satisfied ethyl acetate:toluene=1: 10).

Further, a chloroform solution with 49.0 mg (395 μmol) of p-methoxyphenol was added to the fraction of the silica gel column obtained in the previous step, the resultant was concentrated under a low pressure at a temperature of 30 degrees Celsius or below, and thus the concentrated matters were obtained. Further, the obtained concentrated matters were washed with diethyl ether, and were recovered through filtration. The obtained recovered matters through filtration were dissolved with chloroform. After a chloroform solution with 5.2 mg (equivalent to 500 ppm) of p-methoxyphenol was further added to the resultant, concentration was performed under a low pressure at a temperature of 30 degrees Celsius or below, and the solvent was distillated. With this, a milky white-colored solid matters (the main agent 3 (the compound (iii))) being a target object were obtained. The yield amount was 10.4 g (15.3 mmol), and the yield was 77.6%.

[Formula 34]

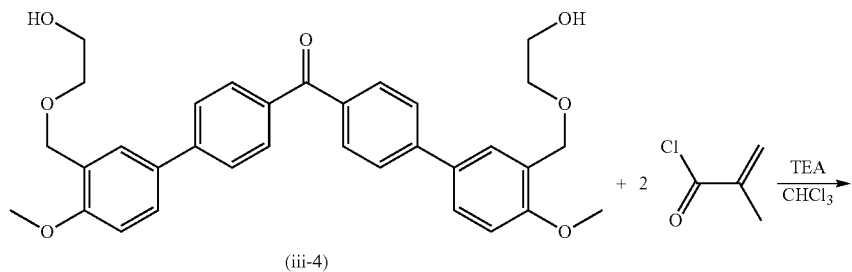

(iii-4)

-continued

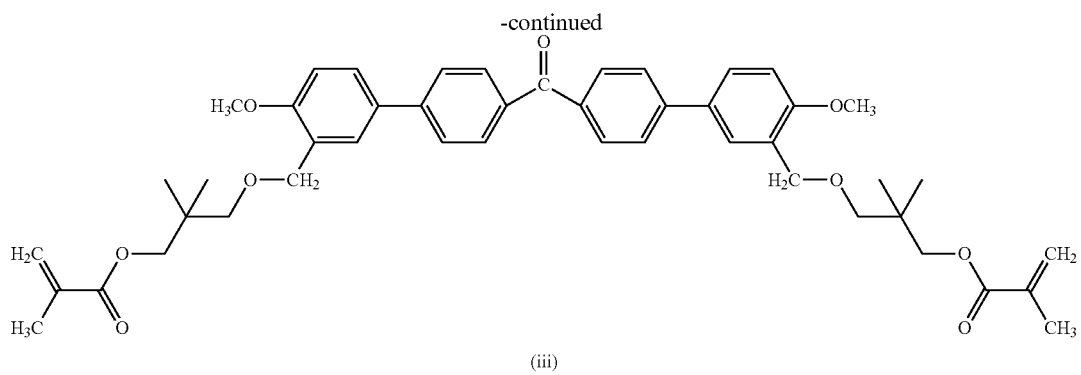

(iii)

Measurement results of ¹H-NMR being the main agent 3 (the compound (iii)) are shown below.

¹H-NMR (300 MHz, DMSO-d6): δ1.86 (6H, s), 3.76 (4H, t), 3.86 (6H, s), 4.30 (4H, t), 4.61 (4H, s), 5.65 and 6.03 (4H, s), 7.13-7.15 (2H, d), 7.71-7.83 (12H, m)

m.p=80 degrees Celsius

Example 7

The compound (1A) and each component forming the curable composition were mixed at a ratio shown in Table 2, and a resin precursor (1A-1) was produced. The obtained resin precursor was in a solution state under an ordinary temperature and pressure. Note that the combination ratios in the table are on a mass % basis unless otherwise noted.

Examples 8 to 13

Each resin precursor was produced similarly to Example 7 except that each component was mixed at a ratio shown in Table 2. A state under an ordinary temperature and pressure was confirmed for each resin precursor.

Components used as a curable composition are described.

[Formula 37]

Main Agent 1
9,9-bis[4-(2-acryloyloxyethoxy)phenyl]fluorene (Formula (i))

[Formula 35]

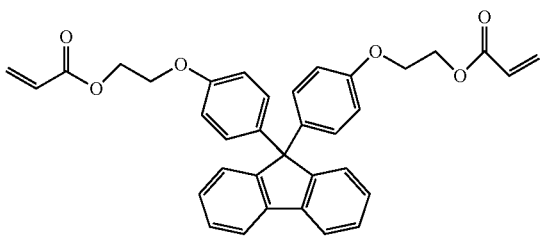

(i)

Main Agent 2
1,6-diacryloyloxy-2,2,3,3,4,4,5,5-octafluorohexane (Formula (ii))

[Formula 36]

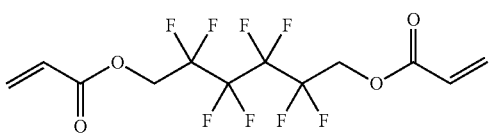

(ii)

Main Agent 3
The compound represented by Formula (iii) given below (Formula ii))

(iii)

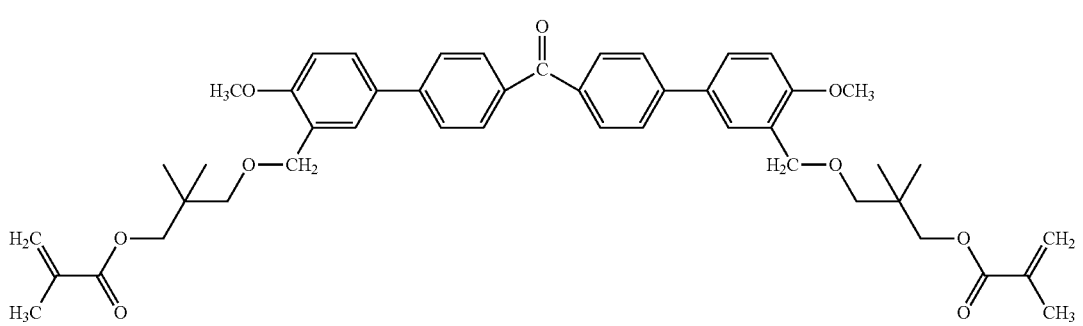

Compatibility Accelerator:

methoxytrypropyleneglycolacrylate (Formula (iv))

[Formula 38]

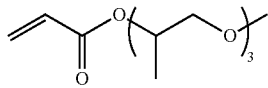
(iv)

Photopolymerization Initiator 1:

1-hydroxy-cyclohexyl-phenyl-ketone (Formula (v))

[Formula 39]

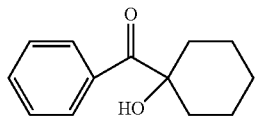
(v)

Photopolymerization Initiator 2:

bis(2-4-6-trimethylbenzoyl)-phenylphosphine oxide (Formula (vi))

[Formula 40]

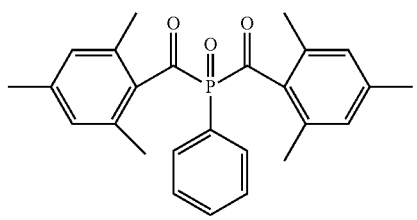
(vi)

Radical Scavenger:

bis(1,2,2,6,6-pentamethyl-4-piperidyl)sebacate (Formula (vii))+methyl 1,2,2,6,6-pentamethyl-4-piperidylsebacate (Formula (viii))

[Formula 41]

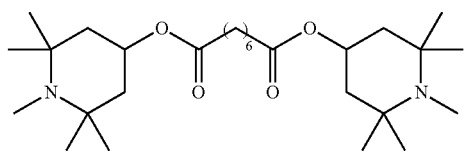
(vii)

[Formula 42]

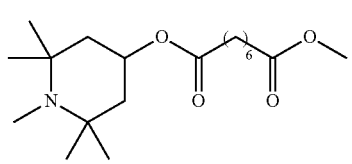
(viii)

Ultraviolet Light Absorber:

2-(2-hydroxy-5-t-octylphenyl)-2H-benzotriazole (Formula (ix))

[Formula 43]

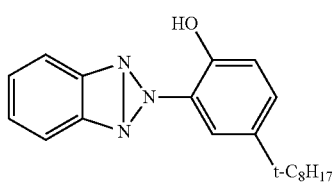
(ix)

<Physical Property Evaluation of Resin Precursor>
(Production of Sample for Refractive Index Measurement)

A physical property of a resin precursor was measured in a liquid state without curing.

(Measurement and Evaluation)

Similarly to the method of measuring a physical property of the compound, refractive indexes $n_C$, $n_d$, $n_F$, and $n_g$ were measured for each resin precursor, and a $\theta_{g,F}$ value and a $v_d$ value were calculated.

TABLE 2

|  | Example 8 | Example 9 | Example 10 | Example 11 | Example 12 | Example 13 |
|---|---|---|---|---|---|---|
|  | \multicolumn{6}{c}{Name of resin precursor} |
|  | 1A-1 | 1A-2 | 1B-1 | 1B-2 | 1F-1 | 1F-2 |
| Compound (1A) | 50 | 40 |  |  |  |  |
| Compound (1B) |  |  | 50 | 40 |  |  |
| Compound (1F) |  |  |  |  | 50 | 40 |
| Main agent 1 (Compound(i)) | 19 | 15.2 | 19 | 15.2 | 19 | 15.2 |
| Main agent 2 (Compound(ii)) | 25.9 | 20.72 | 25.9 | 20.72 | 25.9 | 20.72 |
| Main agent 3 (Compound(iii)) |  | 20 |  | 20 |  | 20 |
| Compatibility accelerator (Compound(iv)) | 2 | 1.6 | 2 | 1.6 | 2 | 1.6 |

TABLE 2-continued

|  | Example 8 | Example 9 | Example 10 | Example 11 | Example 12 | Example 13 |
|---|---|---|---|---|---|---|
|  | | | Name of resin precursor | | | |
|  | 1A-1 | 1A-2 | 1B-1 | 1B-2 | 1F-1 | 1F-2 |
| Photopolymerization 1 initiator (Compound(v)) | 1 | 0.8 | 1 | 0.8 | 1 | 0.8 |
| Photopolymerization 2 initiator (Compound(vi)) | 0.1 | 0.08 | 0.1 | 0.08 | 0.1 | 0.08 |
| Radical scavenger (Compound (vii) + (viii)) | 1 | 0.8 | 1 | 0.8 | 1 | 0.8 |
| Ultraviolet light absorber (Compound (ix)) | 1 | 0.8 | 1 | 0.8 | 1 | 0.8 |
| Total (mass %) | 100 | 100 | 100 | 100 | 100 | 100 |
| State under ordinary temperature and pressure | Liquid | Liquid | Liquid | Liquid | Liquid | Liquid |
| $n_C$ | 1.5320 | 1.5444 | 1.5466 | 1.5550 | 1.5346 | 1.5407 |
| $n_d$ | 1.5384 | 1.5515 | 1.5530 | 1.5620 | 1.5409 | 1.5478 |
| $n_F$ | 1.5547 | 1.5700 | 1.5715 | 1.5818 | 1.5587 | 1.5664 |
| $n_g$ | 1.5706 | 1.5884 | 1.5894 | 1.6017 | 1.5762 | 1.5859 |
| $\theta_{g,F}$ | 0.700 | 0.719 | 0.719 | 0.743 | 0.726 | 0.759 |
| $v_d$ | 23.7 | 21.6 | 22.2 | 21.0 | 22.4 | 21.3 |

III. Production of Cured Object and Physical Property Evaluation

Example 14

The resin precursor (1A-1) was sandwiched between synthetic quartz (t=1 mm), and was irradiated with light from a high luminance mercury xenon lamp ("LC8" manufactured by Hamamatsu Photonics) through a filter cutting a wavelength under 385 nm to be cured. With this, a cured object (1A-1) was obtained.

Examples 15 to 19

Each cured object was obtained similarly to Example 14 except that the resin precursor shown in Table 3 was used. A state under an ordinary temperature and pressure was confirmed for each cured object.

<Physical Property Evaluation of Cured Object>
(Production of Sample for Refractive Index Measurement)

A silicone rubber sheet having a rectangular opening was placed on a quartz glass substrate, and the opening was filled with a resin precursor and then closed with a quartz glass substrate. Subsequently, the resin precursor was irradiated with ultraviolet light through the quartz glass substrate, and was cured. Further, the cured object was released, and a sample for refractive index measurement, which had a shape of 15 mm×15 mm and a thickness of 0.5 mm, was obtained.

(Measurement and Evaluation)

Similarly to the method of measuring a physical property of the compound, refractive indexes $n_C$, $n_d$, $n_F$, and $n_g$ were measured, and a $\theta_{g,F}$ value and an abbe number ($v_d$ value) were calculated.

TABLE 3

|  | Example 14 | Example 15 | Example 16 | Example 17 | Example 18 | Example 19 |
|---|---|---|---|---|---|---|
|  | | | Name of cured object | | | |
|  | 1A-1 | 1A-2 | 18-1 | 18-2 | 1F-1 | 1F-2 |
|  | | | Used resin precursor | | | |
|  | 1A-1 | 1A-2 | 18-1 | 18-2 | 1F-1 | 1F-2 |
| $n_C$ | 1.5527 | 1.5594 | 1.5668 | 1.5726 | 1.5581 | 1.5641 |
| $n_d$ | 1.5590 | 1.5672 | 1.5738 | 1.5803 | 1.5651 | 1.5717 |
| $n_F$ | 1.5759 | 1.5862 | 1.5920 | 1.6005 | 1.5835 | 1.5907 |
| $n_g$ | 1.5923 | 1.6053 | 1.6102 | 1.6213 | 1.6020 | 1.6109 |
| $\theta_{g,F}$ | 0.707 | 0.713 | 0.722 | 0.746 | 0.728 | 0.759 |
| $v_d$ | 24.1 | 21.2 | 22.8 | 20.8 | 22.3 | 21.5 |

It was at least confirmed from above that the compound and the cured object obtained from the resin precursor containing the compound in each example had a high $\theta_{g,F}$ value and a low dispersion characteristic of a refractive index ($v_d$ value).

Examples 20 to 25

Further, for each cured object shown in Table 4, an inner transmittance 27 days after curing and a wavelength at which the inner transmittance was 80% were measured.

(Production of Sample for Transmittance Measurement)

Similarly to the method of producing a sample for refractive index measurement, which is described above, a sample having a thickness of 0.5 mm and a sample having a thickness of 1.0 mm were produced as samples for transmittance measurement for each cured object. Further, the resin precursors that were left to stand for 27 days after curing were used for measurement.

(Evaluation of Inner Transmittance)

A transmittance was measured for the sample having a thickness of 0.5 mm and the sample having a thickness of 1.0 mm, and was corrected in the expression given below. For measurement, a spectrophotometer ("TUV-4700" manufactured by Shimadzu Corporation) was used.

Inner transmittance (>)=$(A/B)^{[100/(a-b)]}$×100

A: Transmittance with a thickness of 1.0 mm
B: Transmittance with a thickness of 0.5 mm a: Actual dimension of a sample having a plate thickness of 1.0 mm
b: Actual dimension of a sample having a plate thickness of 0.5 mm
* Inner transmittance conversion data for 0.5 mm
(Wavelength ($\Delta_{80}$) at which Inner Transmittance was 80%)

First, a sample having a thickness of 12 mm and a sample having a thickness of 2 mm, which were subjected to parallel polishing, were prepared. An inner transmittance was measured in a wavelength range from 200 to 700 nm when light parallel to the thickness direction was incident, and was converted to an inner transmittance for a thickness of 10 mm. Further, a wavelength at which an inner transmittance was 80% was measured as $A_{80}$.

Results indicating an inner transmittance (%) at each wavelength and a wavelength ($\lambda_{80}$; unit nm) at which an inner transmittance was 80% in Examples 20 to 25 are shown in Table 4.

TABLE 4

| | Example 20 | Example 21 | Example 22 | Example 23 | Example 24 | Example 25 |
|---|---|---|---|---|---|---|
| | | | Name of cured object | | | |
| | 1A-1 | 1A-2 | 1B-1 | 1B-2 | 1F-1 | 1F-2 |
| 420 nm | 98% | 91% | 91% | 84% | 97% | 91% |
| 440 nm | 99% | 98% | 98% | 95% | 99% | 97% |
| 460 nm | 100% | 100% | 99% | 96% | 99% | 98% |
| 480 nm | 100% | 100% | 99% | 98% | 100% | 99% |
| 500 nm | 100% | 100% | 99% | 99% | 100% | 99% |
| 550 nm | 100% | 100% | 100% | 100% | 100% | 100% |
| 600 nm | 100% | 100% | 100% | 100% | 100% | 100% |
| 650 nm | 100% | 100% | 100% | 100% | 100% | 100% |
| $\lambda_{80}$ | 405 nm | 413 nm | 414 nm | 418 nm | 405 nm | 413 nm |

REFERENCE SIGNS LIST

1 Imaging device (lens-interchangeable camera)
101 Camera body
102 Lens barrel
103 Lens
104 Sensor chip
105 Glass substrate
106 Multi-chip module
CAM Imaging device (fixed lens camera)
WL Photographing lens
M Liquid crystal monitor
EF Auxiliary light emitting unit
B1 Release button
B2 Function button
2 Multi-photon microscope
201 Pulse laser device
202 Pulse division device
203 Beam adjustment unit
204, 205, 212 Dichroic mirror
206 Objective lens
207, 211, 213 Fluorescence detection unit
208 Condensing lens
209 Pinhole
210 Image forming lens
S Sample
3 Cemented lens
301 First lens element
302 Second lens element
303 Cured object

What is claimed is:

1. A compound represented by Formula (1):

[Formula 1]

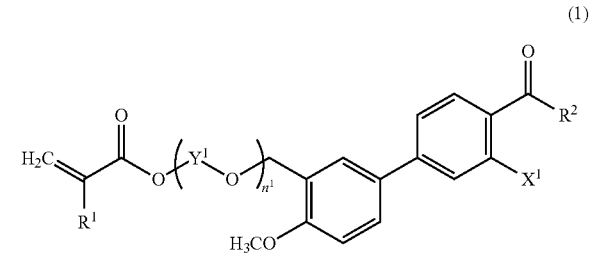

(1)

in the formula, $R^1$ represents a hydrogen atom or a methyl group, $R^2$ represents a hydrogen atom, a phenyl group, a $C_{1-8}$ alkyl group, or a $C_{1-4}$ perfluoroalkyl group, $X^1$ represents a hydrogen atom or a hydroxy group, $Y^1$ represents a $C_{1-9}$ alkylene group optionally substituted with a fluorine atom, and $n^1$ is an integer from 0 to 3.

2. A resin precursor containing the compound according to claim 1 and a curable composition.

3. The resin precursor according to claim 2, wherein the curable composition is a photocurable composition.

4. The resin precursor according to claim 2, wherein the curable composition includes one or more compound selected from a group consisting of a compound represented by Formula (2), a fluorine-containing acrylate compound, a fluorine-containing methacrylate compound, an acrylate compound having a fluorene structure, a methacrylate compound having a fluorene structure, a diacrylate compound, and a dimethacrylate compound;

[Formula 2]

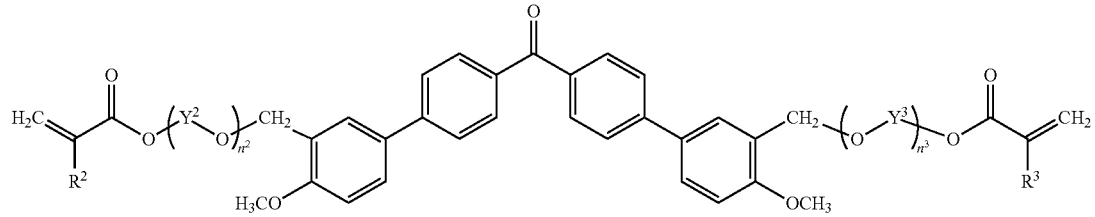

(2)

in the formula, $R^2$ and $R^3$ independently represent a hydrogen atom or a methyl group, $Y^2$ and $Y^3$ independently represent a $C_{1-9}$ alkylene group, and $n^2$ and $n^3$ independently represent an integer from 0 to 3.

5. The resin precursor according to claim 2, wherein the curable composition comprises one or more compound selected from a group consisting of 1,6-diacryloyloxy-2,2,3,3,4,4,5,5-octafluorohexane, 1,6-dimethacryloyloxy-2,2,3,3,4,4,5,5-octafluorohexane, 9,9-bis[4-(2-acryloyloxyethoxy)phenyl]fluorene, and 1,6-hexanediol diacrylate.

6. The resin precursor according to claim 2, wherein the amount of the compound represented by Formula (1) in the resin precursor is 10 to 50 mass %.

7. A cured object obtained by curing the resin precursor according to claim 2.

8. The cured object according to claim 7, having a $\theta_{g,F}$ value is 0.5 or greater.

9. The cured object according to claim 7, having a refractive index ($n_d$) with respect to a d-line is 1.50 or greater and 1.65 or less.

10. The cured object according to claim 7, having an abbe number ($v_d$) is 10 or greater and 40 or less.

11. The cured object according to claim 7, having an inner transmittance is 80% or greater over a wavelength range from 400 nm to 450 nm.

12. An optical element manufactured from the cured object according to claim 7.

13. An optical system comprising the optical element according to claim 12.

14. An interchangeable camera lens comprising the optical system according to claim 13.

15. An optical device comprising the optical system according to claim 13.

16. A cemented lens comprising a first lens element and a second lens element joined with each other through intermediation of the cured object according to claim 7.

17. An optical system comprising the cemented lens according to claim 16.

18. An interchangeable camera lens comprising the optical system according to claim 17.

19. An optical device comprising the optical system according to claim 17.

20. A method for manufacturing a cemented lens, the method comprising:
- a contacting step of contacting a first lens element and a second lens element with each other through intermediation of the resin precursor according to claim 2; and
- a joining step of joining the first lens element and the second lens element with each other by curing the resin precursor.

21. The method for manufacturing a cemented lens according to claim 20, wherein, in the joining step, the resin precursor is irradiated with light to be cured.

22. The method for manufacturing a cemented lens according to claim 21, wherein the light radiates to the resin precursor through the first lens element.

23. The method for manufacturing a cemented lens according to claim 21, wherein the light radiates to the resin precursor through the second lens element.

* * * * *